(12) United States Patent
Ostrovsky et al.

(10) Patent No.: US 9,504,467 B2
(45) Date of Patent: Nov. 29, 2016

(54) LESS TRAUMATIC METHOD OF DELIVERY OF MESH-BASED DEVICES INTO HUMAN BODY

(75) Inventors: Isaac Ostrovsky, Wellesley, MA (US);
Jozef Slanda, Milford, MA (US);
Jianmin Li, Lexington, MA (US);
Brent Palmisano, Fiskdale, MA (US);
James Goddard, Pepperell, MA (US);
Daniel Ostrovsky, Wellesley, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 518 days.

(21) Appl. No.: 12/978,140

(22) Filed: Dec. 23, 2010

(65) Prior Publication Data

US 2011/0152914 A1    Jun. 23, 2011

Related U.S. Application Data

(60) Provisional application No. 61/289,898, filed on Dec. 23, 2009.

(51) Int. Cl.
*A61F 2/00* (2006.01)
*A61B 17/06* (2006.01)
*A61B 17/04* (2006.01)
*A61B 17/00* (2006.01)

(52) U.S. Cl.
CPC ...... *A61B 17/06109* (2013.01); *A61B 17/0482* (2013.01); *A61B 2017/00805* (2013.01); *A61F 2/0045* (2013.01)

(58) Field of Classification Search
CPC .............. A61B 17/06109; A61B 2017/00805; A61B 17/0482; A61F 2/2481; A61F 2/0045
USPC ............ 606/193, 151, 139; 600/37; 604/273
See application file for complete search history.

(56) References Cited

U.S. PATENT DOCUMENTS

| 1,843,272 A | 2/1932 | Evinrude |
| 2,204,265 A | 6/1940 | Wentzel |
| 2,466,282 A | 4/1949 | Sparrow et al. |
| 2,740,260 A | 4/1956 | Blanchard |
| 3,986,363 A | 10/1976 | Beaman et al. |

(Continued)

FOREIGN PATENT DOCUMENTS

| JP | 2001260986 A | 9/2001 |
| JP | 2003098044 A | 4/2003 |

(Continued)

OTHER PUBLICATIONS

Search Report and Written Opinion for International Patent Application No. PCT/US2010/061879, mailed on Mar. 21, 2011, 8 pages.

(Continued)

*Primary Examiner* — Richard Louis
(74) *Attorney, Agent, or Firm* — Brake Hughes Bellermann LLP

(57) ABSTRACT

In some embodiments, a method includes extending a dilator into a body of a patient in a first direction such that a distal end portion of the dilator extends from the body. The dilator defines a lumen therethrough. At least a portion of the dilator is disposed within the body when the distal end portion extends from the body. At least a portion of an implant is passed through the lumen defined by the dilator. The dilator is removed from the body by moving the dilator in the first direction.

16 Claims, 15 Drawing Sheets

(56) References Cited

U.S. PATENT DOCUMENTS

| | | | |
|---|---|---|---|
| 4,412,422 A | 11/1983 | Rossi | |
| 4,622,938 A | 11/1986 | Wenstadt et al. | |
| 4,646,696 A | 3/1987 | Dogadko | |
| 4,648,497 A | 3/1987 | Prince | |
| 4,747,381 A | 5/1988 | Baltz et al. | |
| 4,755,156 A | 7/1988 | Wagner | |
| 4,788,955 A | 12/1988 | Wood | |
| 4,801,282 A | 1/1989 | Ogawa et al. | |
| 4,805,396 A | 2/1989 | Veerhusen et al. | |
| 4,809,506 A | 3/1989 | Lauritsen | |
| 4,810,216 A | 3/1989 | Kawamura | |
| 4,836,809 A | 6/1989 | Pelligrino | |
| 4,850,906 A | 7/1989 | Kanno | |
| 4,858,585 A | 8/1989 | Remmers | |
| 4,898,045 A | 2/1990 | Baba | |
| 4,964,276 A | 10/1990 | Sturdy | |
| 5,004,962 A | 4/1991 | Fonss et al. | |
| 5,051,102 A | 9/1991 | Onoue | |
| 5,062,403 A | 11/1991 | Breckenfeld et al. | |
| 5,062,516 A | 11/1991 | Prince et al. | |
| 5,065,723 A | 11/1991 | Broughton et al. | |
| 5,103,946 A | 4/1992 | Masters et al. | |
| 5,112,344 A | 5/1992 | Petros | |
| 5,157,956 A | 10/1992 | Isaji et al. | |
| 5,167,212 A | 12/1992 | Peter et al. | |
| 5,273,016 A | 12/1993 | Gillespie et al. | |
| 5,318,466 A | 6/1994 | Nagafusa | |
| 5,381,769 A | 1/1995 | Nishigaki et al. | |
| 5,492,493 A | 2/1996 | Ohkita | |
| 5,496,332 A | 3/1996 | Sierra et al. | |
| 5,539,294 A | 7/1996 | Kobayashi | |
| 5,595,159 A | 1/1997 | Huber et al. | |
| 5,611,515 A | 3/1997 | Benderev et al. | |
| 5,664,542 A | 9/1997 | Kanazava et al. | |
| 5,676,670 A | 10/1997 | Kim | |
| 5,730,105 A | 3/1998 | McGinnity | |
| 5,733,325 A | 3/1998 | Robinson et al. | |
| 5,749,343 A | 5/1998 | Nichols et al. | |
| 5,771,860 A | 6/1998 | Bernardi | |
| 5,774,854 A | 6/1998 | Sharman | |
| 5,782,659 A | 7/1998 | Motose | |
| 5,797,920 A | 8/1998 | Kim | |
| 5,798,113 A | 8/1998 | Dionne et al. | |
| 5,800,828 A | 9/1998 | Dionne et al. | |
| 5,800,829 A | 9/1998 | Dionne et al. | |
| 5,834,001 A | 11/1998 | Dionne et al. | |
| 5,837,234 A | 11/1998 | Gentil et al. | |
| 5,842,478 A | 12/1998 | Benderev et al. | |
| 5,860,425 A | 1/1999 | Benderev et al. | |
| 5,865,791 A | 2/1999 | Whayne et al. | |
| 5,869,077 A | 2/1999 | Dionne et al. | |
| 5,871,767 A | 2/1999 | Dionne et al. | |
| 5,874,099 A | 2/1999 | Dionne et al. | |
| 5,891,193 A | 4/1999 | Robinson et al. | |
| 5,899,191 A | 5/1999 | Rabbit et al. | |
| 5,899,909 A | 5/1999 | Claren et al. | |
| 5,935,161 A | 8/1999 | Robinson et al. | |
| 5,984,917 A | 11/1999 | Fleischman et al. | |
| 6,004,347 A | 12/1999 | McNamara et al. | |
| 6,007,544 A | 12/1999 | Kim | |
| 6,015,319 A | 1/2000 | Tanaka | |
| 6,026,783 A | 2/2000 | Nestvall et al. | |
| 6,039,686 A | 3/2000 | Kovac | |
| 6,040,157 A | 3/2000 | Hu et al. | |
| 6,042,534 A | 3/2000 | Gellman et al. | |
| 6,058,349 A | 5/2000 | Kikori et al. | |
| 6,066,325 A | 5/2000 | Wallace et al. | |
| 6,073,509 A | 6/2000 | Salecker et al. | |
| 6,073,592 A | 6/2000 | Brown et al. | |
| 6,077,297 A | 6/2000 | Robinson et al. | |
| 6,083,523 A | 7/2000 | Dionne et al. | |
| 6,095,488 A | 8/2000 | Semeyn, Jr. et al. | |
| 6,098,591 A | 8/2000 | Iwata | |
| 6,109,986 A | 8/2000 | Gaynor et al. | |
| 6,110,101 A | 8/2000 | Tihon et al. | |
| 6,132,438 A | 10/2000 | Fleishman et al. | |
| 6,233,943 B1 | 5/2001 | Beacom et al. | |
| 6,273,771 B1 | 8/2001 | Buckley et al. | |
| 6,280,269 B1 | 8/2001 | Gaynor | |
| 6,322,804 B1 | 11/2001 | Dionne et al. | |
| 6,351,704 B1 | 2/2002 | Koerner | |
| 6,361,559 B1 | 3/2002 | Houser et al. | |
| 6,379,114 B1 | 4/2002 | Schott et al. | |
| 6,379,366 B1 | 4/2002 | Fleischman et al. | |
| 6,382,122 B1 | 5/2002 | Gaynor et al. | |
| 6,385,586 B1 | 5/2002 | Dietz | |
| 6,414,607 B1 | 7/2002 | Gonring et al. | |
| 6,423,080 B1 | 7/2002 | Gellman et al. | |
| 6,587,765 B1 | 7/2003 | Graham et al. | |
| 6,599,302 B2 | 7/2003 | Houser et al. | |
| 6,612,882 B2 | 9/2003 | Shidara et al. | |
| 6,689,047 B2 | 2/2004 | Gellman | |
| 6,689,062 B1 | 2/2004 | Mesallum | |
| 6,704,643 B1 | 3/2004 | Suhre et al. | |
| 6,719,781 B1 | 4/2004 | Kim | |
| 6,734,285 B2 | 5/2004 | Hu et al. | |
| 6,740,101 B2 | 5/2004 | Houser et al. | |
| 6,751,533 B2 | 6/2004 | Graham et al. | |
| 6,752,814 B2 | 6/2004 | Gellman et al. | |
| 6,830,052 B2 | 12/2004 | Carter et al. | |
| 6,830,576 B2 | 12/2004 | Fleishman et al. | |
| 6,843,795 B1 | 1/2005 | Houser et al. | |
| 6,887,249 B1 | 5/2005 | Houser et al. | |
| 6,910,927 B2 | 6/2005 | Kanno | |
| 6,960,351 B2 | 11/2005 | Dionne et al. | |
| 6,965,817 B2 | 11/2005 | Graham et al. | |
| 7,014,607 B2 | 3/2006 | Gellman | |
| 7,101,366 B2 | 9/2006 | Trout, III et al. | |
| 7,121,908 B2 | 10/2006 | Okuyama | |
| 7,142,955 B1 | 11/2006 | Kern et al. | |
| 7,153,174 B2 | 12/2006 | Takada et al. | |
| 7,153,942 B2 | 12/2006 | Hu et al. | |
| 7,156,863 B2 | 1/2007 | Sonnenschein et al. | |
| 7,182,771 B1 | 2/2007 | Houser et al. | |
| 7,186,688 B1 | 3/2007 | Hu et al. | |
| 7,208,582 B2 | 4/2007 | Rosen et al. | |
| 7,220,153 B2 | 5/2007 | Okuyama | |
| 7,235,094 B2 | 6/2007 | Serino et al. | |
| 7,273,751 B2 | 9/2007 | Coleman | |
| 7,297,144 B2 | 11/2007 | Fleishman et al. | |
| 7,303,525 B2 | 12/2007 | Watschke et al. | |
| 7,377,938 B2 | 5/2008 | Sarac et al. | |
| 7,393,320 B2 | 7/2008 | Montpetit et al. | |
| 7,402,312 B2 | 7/2008 | Rosen et al. | |
| 7,413,540 B2 | 8/2008 | Gellman et al. | |
| 7,439,333 B2 | 10/2008 | Hu et al. | |
| 7,485,092 B1 | 2/2009 | Stewart et al. | |
| 7,524,281 B2 | 4/2009 | Chu et al. | |
| 7,572,257 B2 | 8/2009 | Whayne et al. | |
| 7,578,839 B2 | 8/2009 | Serino et al. | |
| 2001/0018549 A1 | 8/2001 | Scetbon | |
| 2001/0056282 A1 | 12/2001 | Sonnenschein et al. | |
| 2002/0193448 A1 | 12/2001 | Wallace et al. | |
| 2002/0032462 A1 | 3/2002 | Houser et al. | |
| 2002/0055748 A1 | 5/2002 | Gellman et al. | |
| 2002/0058959 A1* | 5/2002 | Gellman | A61B 17/0401 606/185 |
| 2002/0082627 A1 | 6/2002 | Berg et al. | |
| 2002/0090388 A1 | 7/2002 | Humes et al. | |
| 2002/0090389 A1 | 7/2002 | Humes et al. | |
| 2002/0099258 A1* | 7/2002 | Staskin | A61B 17/3468 600/29 |
| 2002/0099394 A1 | 7/2002 | Houser et al. | |
| 2002/0111636 A1 | 8/2002 | Fleischman et al. | |
| 2002/0150603 A1 | 10/2002 | Dionne et al. | |
| 2002/0156487 A1 | 10/2002 | Gellman et al. | |
| 2002/0156488 A1 | 10/2002 | Gellman et al. | |
| 2002/0173808 A1 | 11/2002 | Houser et al. | |
| 2002/0173809 A1 | 11/2002 | Fleischman et al. | |
| 2003/0008357 A1 | 1/2003 | Hu et al. | |
| 2003/0028007 A1 | 2/2003 | Hu et al. | |
| 2003/0033005 A1 | 2/2003 | Houser et al. | |
| 2003/0062052 A1 | 4/2003 | Carter et al. | |
| 2003/0082962 A1 | 5/2003 | Kanno | |

(56) References Cited

U.S. PATENT DOCUMENTS

| | | |
|---|---|---|
| 2003/0092331 A1 | 5/2003 | Okuyama |
| 2003/0093196 A1 | 5/2003 | Okuyama |
| 2003/0167064 A1 | 9/2003 | Whayne |
| 2003/0170786 A1 | 9/2003 | Rosen et al. |
| 2003/0175274 A1 | 9/2003 | Rosen et al. |
| 2003/0176674 A1 | 9/2003 | Rosen et al. |
| 2003/0176875 A1* | 9/2003 | Anderson et al. ............ 606/151 |
| 2003/0195607 A1 | 10/2003 | Trout et al. |
| 2003/0212305 A1* | 11/2003 | Anderson et al. ............ 600/29 |
| 2003/0215921 A1 | 11/2003 | Coleman |
| 2004/0002679 A1 | 1/2004 | Trout et al. |
| 2004/0029461 A1 | 2/2004 | Shomura |
| 2004/0039246 A1 | 2/2004 | Gellman et al. |
| 2004/0064014 A1 | 4/2004 | Melvin et al. |
| 2004/0078053 A1 | 4/2004 | Berg et al. |
| 2004/0097801 A1 | 5/2004 | Mesallum |
| 2004/0097993 A1 | 5/2004 | Whayne |
| 2004/0106845 A1* | 6/2004 | Anderson et al. ............ 600/30 |
| 2004/0106846 A1* | 6/2004 | Gellman ........................ 600/30 |
| 2004/0111145 A1 | 6/2004 | Serino et al. |
| 2004/0116944 A1 | 6/2004 | Chu et al. |
| 2004/0143103 A1 | 7/2004 | Hu et al. |
| 2004/0185083 A1 | 9/2004 | Dionne et al. |
| 2004/0199177 A1 | 10/2004 | Kim |
| 2004/0225181 A1* | 11/2004 | Chu et al. ........................ 600/37 |
| 2004/0230206 A1 | 11/2004 | Gellman et al. |
| 2004/0230207 A1 | 11/2004 | Gellman et al. |
| 2004/0236314 A1 | 11/2004 | Saab |
| 2004/0236411 A1 | 11/2004 | Sarac et al. |
| 2005/0033321 A1 | 2/2005 | Fleischman et al. |
| 2005/0043580 A1 | 2/2005 | Watschke et al. |
| 2005/0059117 A1 | 3/2005 | Rosen et al. |
| 2005/0090706 A1 | 4/2005 | Gellman et al. |
| 2005/0110214 A1 | 5/2005 | Shank et al. |
| 2005/0113904 A1 | 5/2005 | Shank et al. |
| 2005/0118895 A1 | 6/2005 | Kanno et al. |
| 2005/0148818 A1 | 7/2005 | Mesallum |
| 2005/0176103 A1 | 8/2005 | Hu et al. |
| 2005/0192429 A1 | 9/2005 | Rosen et al. |
| 2005/0197525 A1 | 9/2005 | Gellman |
| 2005/0232921 A1 | 10/2005 | Rosen et al. |
| 2005/0245145 A1 | 11/2005 | Takada et al. |
| 2005/0245787 A1* | 11/2005 | Cox et al. ........................ 600/37 |
| 2005/0251244 A1 | 11/2005 | Vounderwalde |
| 2005/0267325 A1 | 12/2005 | Bouchier et al. |
| 2005/0286539 A1 | 12/2005 | Okuyama |
| 2006/0025331 A1 | 2/2006 | Hu et al. |
| 2006/0025649 A1* | 2/2006 | Smith et al. ............ 600/30 |
| 2006/0041185 A1* | 2/2006 | Browning ........................ 600/37 |
| 2006/0057117 A1 | 3/2006 | Coleman |
| 2006/0074484 A1 | 4/2006 | Huber |
| 2006/0122620 A1 | 6/2006 | Kim |
| 2006/0161110 A1 | 7/2006 | Lenker et al. |
| 2006/0177478 A1 | 8/2006 | Humes et al. |
| 2006/0195011 A1 | 8/2006 | Arnal et al. |
| 2006/0229493 A1* | 10/2006 | Weiser ............ A61B 17/00234 600/37 |
| 2006/0240720 A1 | 10/2006 | Yamashita et al. |
| 2006/0253132 A1 | 11/2006 | Evans et al. |
| 2006/0253152 A1 | 11/2006 | Evans et al. |
| 2006/0258898 A1 | 11/2006 | Montpetit et al. |
| 2006/0260618 A1* | 11/2006 | Hodroff ........... A61B 17/06066 128/830 |
| 2006/0287673 A1 | 12/2006 | Brett et al. |
| 2006/0293646 A1 | 12/2006 | Whayne et al. |
| 2007/0010807 A1 | 1/2007 | Chu |
| 2007/0010830 A1 | 1/2007 | Gellman et al. |
| 2007/0010875 A1 | 1/2007 | Trout et al. |
| 2007/0021649 A1 | 1/2007 | Nowlin et al. |
| 2007/0021760 A1 | 1/2007 | Kelleher |
| 2007/0043374 A1 | 2/2007 | Evans |
| 2007/0060788 A1 | 3/2007 | Gellman |
| 2007/0082565 A1 | 4/2007 | Okuyama |
| 2007/0092489 A1 | 4/2007 | Fishbein et al. |
| 2007/0129751 A1 | 6/2007 | Muni et al. |
| 2007/0149999 A1 | 6/2007 | Szabo et al. |
| 2007/0173926 A1 | 7/2007 | Bobo et al. |
| 2007/0178780 A1 | 8/2007 | Ito et al. |
| 2007/0203517 A1 | 8/2007 | Williams et al. |
| 2007/0218785 A1 | 9/2007 | Okuyama et al. |
| 2007/0219620 A1 | 9/2007 | Eells et al. |
| 2007/0225642 A1 | 9/2007 | Houser et al. |
| 2007/0227429 A1 | 10/2007 | Okuyama et al. |
| 2007/0232162 A1 | 10/2007 | Okuyama et al. |
| 2007/0249244 A1 | 10/2007 | Watanable et al. |
| 2007/0250222 A1 | 10/2007 | Okuyama et al. |
| 2007/0270055 A1 | 11/2007 | Ito et al. |
| 2007/0282490 A1 | 12/2007 | Ito et al. |
| 2007/0293102 A1 | 12/2007 | Okuyama et al. |
| 2008/0003898 A1 | 1/2008 | Watanabe et al. |
| 2008/0009747 A1 | 1/2008 | Saadat et al. |
| 2008/0015569 A1 | 1/2008 | Saadat et al. |
| 2008/0033457 A1 | 2/2008 | Francischelli et al. |
| 2008/0046005 A1 | 2/2008 | Lenker et al. |
| 2008/0066769 A1 | 3/2008 | Dineen et al. |
| 2008/0077174 A1 | 3/2008 | Mische |
| 2008/0097487 A1 | 4/2008 | Pool et al. |
| 2008/0097488 A1 | 4/2008 | Fleischman et al. |
| 2008/0097496 A1 | 4/2008 | Chang et al. |
| 2008/0125621 A1* | 5/2008 | Gellman et al. ............... 600/37 |
| 2008/0125791 A1 | 5/2008 | Gellman et al. |
| 2008/0146867 A1 | 6/2008 | Gellman et al. |
| 2008/0187604 A1 | 8/2008 | Tomaselli et al. |
| 2008/0199541 A1 | 8/2008 | Tomaselli et al. |
| 2008/0221386 A1 | 9/2008 | Gellman et al. |
| 2008/0269552 A1 | 10/2008 | Montpetit et al. |
| 2008/0286250 A1 | 11/2008 | Tornoe et al. |
| 2008/0286288 A1 | 11/2008 | Rosen et al. |
| 2008/0286323 A1 | 11/2008 | Tornoe et al. |
| 2008/0287740 A1 | 11/2008 | Weitzner et al. |
| 2009/0018387 A1 | 1/2009 | Veronikis |
| 2009/0023224 A1 | 1/2009 | Rosenig et al. |
| 2009/0023986 A1 | 1/2009 | Stewart et al. |
| 2009/0024072 A1 | 1/2009 | Criado et al. |
| 2009/0043356 A1 | 2/2009 | Longhini et al. |
| 2009/0054970 A1 | 2/2009 | Houser et al. |
| 2009/0093672 A1* | 4/2009 | Chu .................. A61B 17/06109 600/37 |
| 2009/0104248 A1 | 4/2009 | Rapacki et al. |
| 2009/0132025 A1 | 5/2009 | Shank et al. |
| 2009/0137861 A1 | 5/2009 | Goldberg et al. |
| 2009/0143789 A1 | 6/2009 | Houser |
| 2009/0143808 A1 | 6/2009 | Houser |
| 2009/0156891 A1 | 6/2009 | Heys et al. |
| 2009/0171139 A1 | 7/2009 | Chu |
| 2009/0171140 A1* | 7/2009 | Chu .................. A61B 17/0482 600/37 |
| 2009/0192347 A1* | 7/2009 | Davila et al. .................... 600/37 |
| 2009/0198172 A1 | 8/2009 | Garrison et al. |
| 2010/0198003 A1* | 8/2010 | Morningstar et al. .......... 600/37 |

FOREIGN PATENT DOCUMENTS

| | | |
|---|---|---|
| JP | 2003127986 A | 5/2003 |
| JP | 2003146293 A1 | 5/2003 |
| JP | 2004068704 A | 3/2004 |
| JP | 2004244003 A | 9/2004 |
| JP | 2005297785 A | 10/2005 |
| WO | 2004/016180 A2 | 2/2004 |
| WO | 2005/102833 A1 | 11/2005 |
| WO | 2011/079222 A2 | 6/2011 |

OTHER PUBLICATIONS

"Suprapubic Mid-Urethral Sling System", Lynx, Boston Scientific, Apr. 29, 2004, 4 pages.

"Solyx SIS Systems: The Carrier Tip that Allows for Advanced Control", Boston Scientific, Copyright 2009, retrieved on Oct. 22, 2009 from http://www.bostonscientific.com, 2 pages.

"Solyx SIS Systems: Advanced Control with Micro Adjustability", Boston Scientific, Copyright 2009, 4 pages.

(56) References Cited

OTHER PUBLICATIONS

"Advantage: Transvaginal Mid-Urethral Sling System", Boston Scientific, Copyright 2003, 4 pages.

Kohli, "A Minimally Invasive Approach to Anterior Wall Reconstruction for Incontinence and Prolapse: Four Corner Cystocele Repair With Repliform Graft Combined with Advantage Mid-Urethral Sling", Boston Scientific, Copyright 2004, 4 pages.

"Advantage: Transvaginal Mid-Urethral Sling System", Boston Scientific, Copyright 2009, retrieved on Oct. 22, 2009 from http://www.bostonscientific.com, 2 pages.

Kleeman, Steve, "Obtryx: Transobturator System Featuring Advantage Mesh", Boston Scientific, Copyright 2006, 4 pages.

"Obtryx: Transobturator Mid-Urethral Sling System", Boston Scientific, Copyright 2009, retrieved on Oct. 22, 2009 from http://www.bostonscientific.com, 2 pages.

"Obtryx: Transobturator Mid-Urethral Sling System", Boston Scientific, Copyright 2008, 4 pages.

Leach, "Obtryx Sling System", Boston Scientific, Copyright 2006, 4 pages.

Nilsson, C. G., et al., "The Tension-free Vaginal Tape Procedure is Successful in the Majority of Women with Indications for Surgical Treatment of Urinary Stress Incontinence", British Journal of Obstetrics and Gynecology, vol. 108, Apr. 2001, pp. 414-419.

Atherton, M. J., et al., "A Comparison of Bladder Neck Movement and Elevation After Tension-free Vaginal Tape and Colposuspension", British Journal of Obstetrics and Gynecology, vol. 107, Nov. 2000, pp. 1366-1370.

Ulmsten, et al., "An Ambulatory Surgical Procedure Under Local Anesthesia for Treatment of Female Urinary Incontinence", International Urogynecology Journal, vol. 7, No. 2, 1996, pp. 81-86.

\* cited by examiner

LESS TRAUMATIC METHOD OF DELIVERY OF MESH-BASED DEVICES INTO HUMAN BODY

RELATED APPLICATION

This application claims priority to and the benefit of U.S. Provisional Patent Application Ser. No. 61/289,898, filed on Dec. 23, 2009, entitled, "Less Traumatic Method of Delivery of Mesh-Based Devices Into Human Body," which is incorporated herein by reference in its entirety.

BACKGROUND

The disclosed invention relates generally to medical devices and more particularly to implants and less traumatic methods for delivering implants within a pelvic region of a patient to treat various pelvic dysfunctions.

A variety of medical procedures are performed to treat various female pelvic dysfunctions, including procedures to treat urinary incontinence, and correcting various prolapse conditions such as uterine prolapse, cystoceles, rectoceles, and vaginal vault prolapse.

Women often experience vaginal prolapses due to age or other factors. For example, women may experience a cystocele, a rectocele and/or a hysterocele. A cystocele occurs when the bladder bulges into the vagina, and a rectocele occurs when the rectum bulges into the vagina. A hysterocele occurs when the uterus descends into the vagina. An enterocele small bowel prolapse) can also occur, when the small bowel pushes through the upper wall of the vagina. It is relatively common for a hysterocele and cystocele or hysterocele and rectocele, or other combinations thereof to occur at the same time. It is also common for different types of prolapse to occur in relatively quick succession.

Treatment has included suturing procedures or the use of implants for support or suspension. A hysterocele is often treated with a hysterectomy followed by a vaginal vault suspension. Various devices and procedures are used to deliver and secure pelvic implants within a variety of different anatomical structures within a pelvic region. Implants can be delivered to a pelvic region through one or more vaginal incisions, and/or through exterior incisions in the patient.

Known methods of delivering or implanting implants, such as slings, within the body include the use sleeves. In such known methods, a sleeve is disposed about the implant during insertion such that the sleeve and the implant are inserted within a bodily tissue. The sleeve, with the implant inside, is inserted through a bodily tissue. Once the implant is, for example, in a desired positioned within the bodily tissue, the sleeve can be removed from the body leaving the implant disposed within the bodily tissue. The sleeve protects the tissue from abrasion by the implant during delivery and adjustment, and protects the implant from over-stretching during delivery. The use of such known sleeves during implantation, however, can result in trauma to the bodily tissue through which the sleeve and implant have been inserted. More specifically, the sleeve adds bulk to the implant, and is typically stiffer than the implant, requiring larger incisions needed and/or holes created within the bodily tissue (for example, double the size). Undesirably large forces may also be required to pull the sleeved implant through a bodily tissue.

Thus, a need exists for a medical device that reduces trauma to the bodily tissue during insertion of an implant, i.e. by reducing the required size of the incision and/or the hole through the tissue. Also, a need exists for a medical device that reduces the force required to move the device through the bodily tissue.

SUMMARY

In some embodiments, a method includes extending a dilator into a body of a patient in a first direction such that a distal end portion of the dilator extends from the body. The dilator defines a lumen therethrough. At least a portion of the dilator is disposed within the body when the distal end portion extends from the body. At least a portion of an implant is passed through the lumen defined by the dilator. The dilator is removed from the body by moving the dilator in the first direction.

DETAILED DESCRIPTION

The devices and methods described herein are generally directed to implants (e.g., slings for treatment of incontinence, such as by bladder neck suspension, posterior support implants, anterior support implants, and total pelvic floor repair implants) and the delivery and placement of such implants within a pelvic region of a patient using one or more dilators. An implant can be placed into the pelvic space of a patient and secured at one or more locations within the pelvic space to treat many different female pelvic floor dysfunctions.

The insertion device (i.e., the one or more dilators) is configured to place, deposit, or otherwise insert an implant (e.g., a sling) into one or more bodily tissues of a patient. The implant is configured to suspend or support a bodily tissue or organ when the implant is retained within the patient through tissue ingrowth and/or temporary suturing. For example, in one embodiment, the insertion device can place the implant under the bladder neck through the both obturator externus muscles and further through corresponding skin incisions for incontinence treatment.

As used in this specification, unless otherwise apparent from the context, the words "proximal" and "distal" refer to the direction closer to and further away from, respectively, an operator (e.g., surgeon, physician, nurse, technician, etc) who would use an insertion device during a procedure. For example, the end of an insertion device first to contact the patient's body would be the distal end, while the opposite end of the insertion device (e.g., the end of the insertion device being operated by the operator) would be the proximal end of the insertion device. Similarly, the end of a insertion device implanted the furthest within the patient's body would be the distal end, while the opposite end of the insertion device (e.g., the end of the insertion device that is inserted the least amount within the body or the end of the insertion device that is disposed outside of the body) would be the proximal end.

Figure 1:
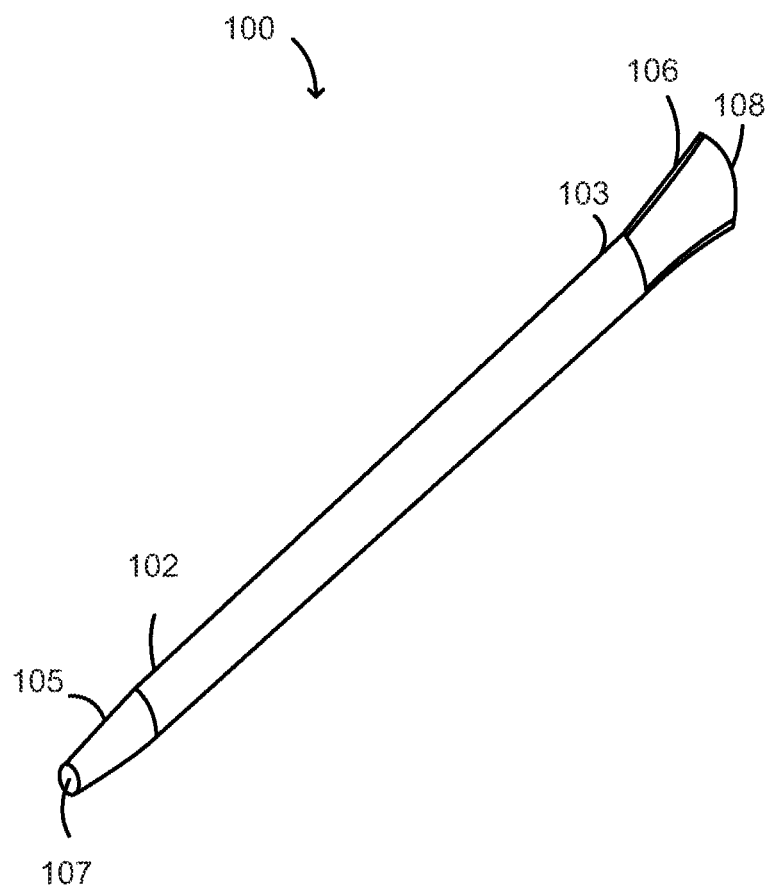
FIG. 1 is a schematic illustration of a dilator according to an embodiment.

FIG. 1 is a schematic illustration of a dilator 100 configured to be inserted within a body of a patient and to deliver an implant within the body. The dilator 100, which can be, for example, a tube, includes a proximal end portion 103 and a distal end portion 102. Additionally, the dilator 100 defines a distal opening 107, a proximal opening 108 and a lumen (not identified) extending therethrough. The distal opening 107 is in fluid communication with the proximal opening 108 via the lumen. The lumen is configured to receive at least a portion of an implant (not illustrated) via the distal opening 107 and/or the proximal opening 108, as described herein. The lumen is also configured to receive at least a portion of a delivery needle (not illustrated) via the distal opening 107 and/or the proximal opening 108, as described herein.

The distal end portion 102 of the dilator 100 is configured to be inserted into a bodily tissue through an incision. Such a bodily tissue can be, for example, a vaginal tissue, an obturator membrane, a supra-pubic tissue, a retro-pubic tissue and/or the like. The distal end portion 102 of the dilator 100 may include a tapered tip 105. The tapered tip 105 is configured to allow the dilator 100 to advance through the bodily tissue more easily. Said another way, the tapered tip 105 facilitates a smooth insertion of the dilator 100 into the bodily tissue. The tapered tip 105 can be tapered at any suitable angle (or rate) to reduce tissue resistance during insertion.

The proximal end portion 103 of the dilator 100 includes an enlarged portion 106. The enlarged portion 106, which may have, for example, a cone shape, is configured to operate as a funnel for the dilator 100. For example, the enlarged portion 106 can receive, via the proximal opening 108, a portion of an implant having a lateral dimension larger than a diameter of the lumen. The enlarged portion 106 can facilitate advancing the implant through the lumen by enabling the implant to gradually contract to a dimension sufficient to fit through the lumen without the exertion of undue force on the dilator 100 and/or the implant. In some instances, when the proximal end portion 103 of the dilator 100 is extended through a bodily tissue, the enlarged portion 106 provides a surgeon (or other doctor) a larger area with which to perform a procedure. The enlarged portion 106 can increase at any suitable angle (or rate). Although the enlarged portion 106 is illustrated and described above as having a cone shape (i.e., a circular funnel shape), in other embodiments, the enlarged portion 106 can have any suitable shape and/or size. For example, in some embodiments, the enlarged portion 106 can have a flat funnel shape. In some embodiments, however, the dilator 106 does not include an enlarged portion 106.

In use, the dilator 100 is configured to engage a delivery needle (e.g., delivery needle 230 or 330 shown in FIGS. 2 and 3, respectively) prior to insertion into the body. The delivery needle is configured to either push or pull the dilator 100 through an incision and into the body, as described in more detail herein. In one example, the delivery needle can push the dilator 100 through a vaginal incision. The delivery needle can further push the distal end portion 102 of the dilator 100 through the pelvic region of the body (including, for example, the retropubic space or the obturator foramens) and out of a skin incision, e.g. suprapubic or perineal. In such an example, the dilator 100 is positioned within the body such that the proximal end portion 103 is disposed flush with the first layer of tissue in which the implant is to be anchored and the distal end portion 102 is disposed through the skin incision, extending from the body.

Once the dilator 100 is positioned within the body, the delivery needle is disengaged from the dilator 100 and a portion of an implant can be advanced through the lumen of the dilator 100. The implant can be, for example, a mesh sling or a mesh tape having a flat configuration or a rolled configuration. In some embodiments, a portion of the implant can be pushed through the dilator 100 in a distal direction via a pusher. In some embodiments, a portion of the implant can be coupled to a suture such that the suture is passed distally through the lumen and out of the distal opening 107 of the dilator 100. The surgeon, for example, can then pull the suture and guide the implant into the lumen of the dilator 100 via the suture.

Once a suitable portion of the implant is disposed within the dilator 100, the implant can be adjusted and/or tensioned. Since the length of the dilator 100 is sufficient to extend through body tissue from an entrance incision (e.g., in tissue in the pelvic region, accessed via a vaginal incision) to an exit incision (e.g. the supra-pubic incision), the implant can be inserted and positioned within the body within the dilator 100 without contacting any portion of the body other than the desired tissue or organ the implant is configured to support, as described in more detail herein. It should be understood that, although the procedure described above refers to only one dilator 100, insertion of an implant, such as a sling, often involves the use of two dilators (see, for example, FIG. 9). For example, the dilator 100 can be used to implant a right portion of a sling and another dilator can be used to implant a left portion of the sling such that a body portion of the sling is disposed beneath and supports a bladder neck. In such an example, the dilator 100 extends through tissue in the retropubic region and a right supra-pubic incision, while the other dilator extends through tissue in the retropubic region and a left supra-pubic incision. Thus, an adjustment or tensioning of the sling can include adjusting the right portion of the sling relative to the left portion of the sling such that the body portion of the sling is properly tensioned to support the bladder neck.

The dilator 100 can be removed from the body after the implant is positioned within the body (albeit within the dilator 100, which is within the body). The implant remains within the body and now contacts the bodily tissue between the supra-pubic incision site and the internal tissue incision. The vaginal incision can then be closed via suturing and/or the like. The portion of the implant extending from the external (e.g. supra-pubic) incision can be trimmed off, and the external incision can also be closed (with the portion of the implant disposed therein) via suturing and/or the like. In some embodiments, the dilator 100 can be removed from the body by moving the dilator 100 in the distal direction (i.e., the same direction as the insertion). In this manner, the proximal end portion 103 of the dilator 100 exits the body via the skin incision.

The dilator 100 can have any suitable shape and/or size. The dilator 100 can be constructed of any suitable, biocompatible material configured to be disposed within the body. For example, the dilator 100 can be constructed of a substantially rigid material, such as a stainless steel. In some embodiments, the dilator 100 can be constructed of a polymer. The dilator 100 can be formed, for example, by molding, extruding, casting, sintering, forging, machining, or other known methods of manufacturing, such medical devices.

The dilator 100 can have a substantially smooth and/or continuous outer surface to prevent or reduce friction produced between the dilator 100 and the bodily tissue when the dilator 100 contacts the bodily tissue during insertion. As friction between the dilator 100 and the bodily tissue decreases, the amount of force required to insert or move the dilator 100 through the bodily tissue decreases. Thus, the likelihood of damaging the bodily tissue during insertion also decreases.

In some embodiments, the distal end portion 102 of the dilator 100 can include an aperture (not illustrated in the embodiment of FIG. 11, but illustrated, for example in the embodiment of FIG. 9) through which a suture can extend. For example, as described above, the implant can be coupled to a suture such that the suture is passed through the dilator 100 and used to pull or guide the implant through the dilator 100. In this embodiment, an end of the suture can be laced through the aperture and, for example, tied to the distal end portion 102 of the dilator 100 such that the suture is releasably coupled to the dilator 100 before insertion. In this manner, the dilator 100 is inserted within the body along with the suture. When the surgeon, for example, is ready to move the implant into the dilator 100, the suture can be decoupled untied), removed from the aperture and pulled in the same manner described above. In some embodiments, however, the suture can be fixedly coupled within the aperture and/or a distal end potion 102 of the dilator 100.

Figure 2:
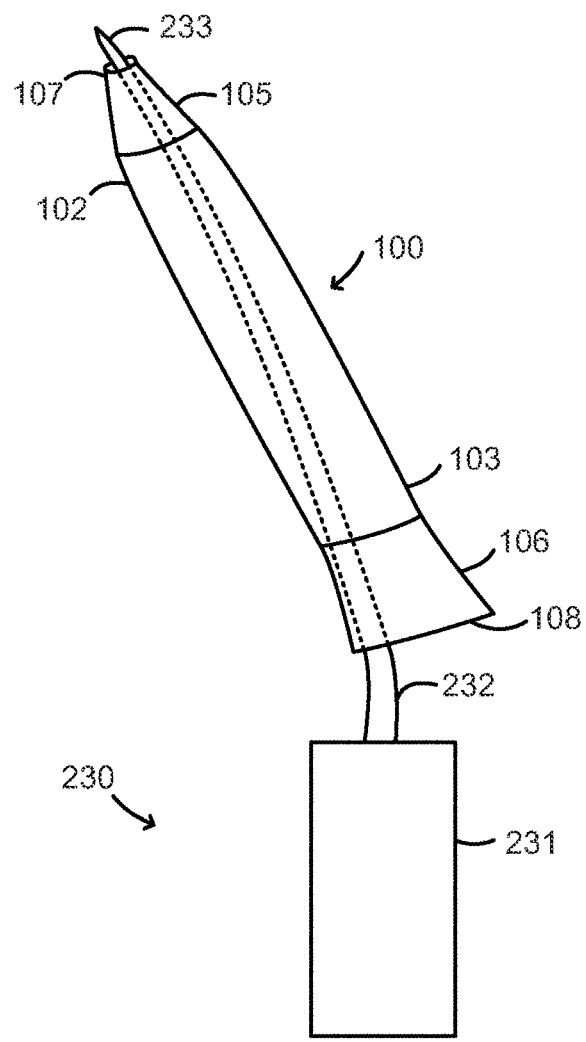
FIG. 2 is a schematic illustration of a delivery needle coupled to the dilator in FIG. 1 according to an embodiment.

FIG. 2 is schematic illustration of the dilator 100 coupled to a delivery needle 230 prior to insertion into a body. The delivery needle 230 is configured to push the dilator 100 through the body. The method of inserting the dilator 100 via the delivery needle 230, as disclosed below, is herein referred to as the "push" method. The delivery needle 230 includes a handle 231 and a needle 232 with a tip 233. The needle 232, which has a slight curvature along its length, is coupled to the handle 231.

When the delivery needle 230 is coupled to the dilator 100, the needle 232 is disposed within the lumen defined by the dilator 100 such that the tip 233 of the needle 232 extends from the distal opening 107 of the dilator 100. In some embodiments, the tip 233 and/or another portion of the needle 232 can form an interference fit with the dilator 100 when the needle 232 is disposed within the distal opening 107. In this manner, the dilator 100 can be restricted from moving or uncoupling from the delivery needle 230 during insertion. On other embodiments, however, the needle 232 can be coupled to the dilator 100 in any other suitable manner.

In use, the delivery needle 230 is coupled to the dilator 100 in the manner described above, and inserted into the body, for example, via a vaginal incision. The delivery needle 230 can be operated, for example, by a surgeon. The delivery needle 230 is pushed through the body toward, for example, a supra-pubic incision, such that the dilator 100 is pushed through body tissue toward the supra-pubic incision. In some embodiments, the delivery needle 230 can be pushed through the body toward, for example, a retro-pubic incision, a perineum incision and/or the like. Additionally, in some embodiments, pushing the delivery needle 230 through the body includes pushing the delivery needle 230 and a portion of the dilator 100 through an obturator membrane.

The advancement of the delivery needle 230 through the body is halted after the tip 233 of the delivery needle 230 reaches the supra-pubic incision (or other desired incision) and the distal end portion 102 of the dilator 100 extends from the body through the supra-pubic incision (or other desired incision), once the proximal opening 108 of the dilator is approximately flush with the body tissue into which the dilator 100 has been inserted. The delivery needle 230 can then be uncoupled from the dilator 100 and removed from the body. The delivery needle 230 is removed by moving (or pulling) the needle 232 in the opposite direction from which it was pushed through the body. In this manner, the delivery needle 230 is removed from the vaginal incision (i.e., the same incision through which it was inserted). The dilator 100 remains within the body.

Figure 3:
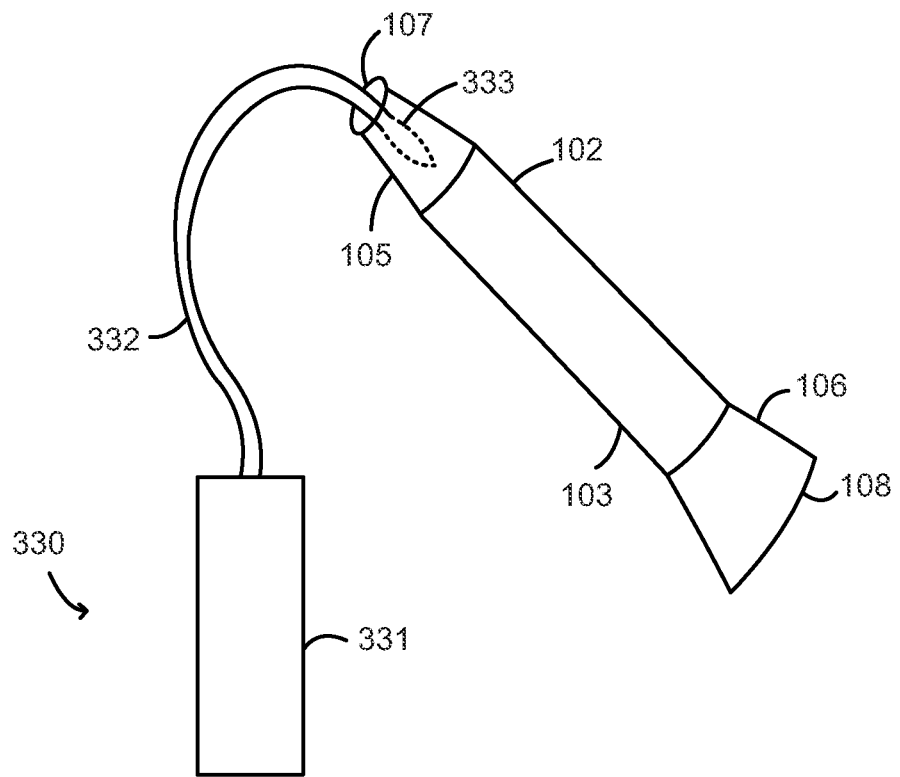
FIG. 3 is a schematic illustration of a delivery needle coupled to the dilator in FIG. 1 according to another embodiment.

FIG. 3 is a schematic illustration of the dilator 100 coupled to a delivery needle 330 during insertion into a body. The delivery needle 330 is configured to pull the dilator 100 through the body tissue. Thus, as will be described in more detail herein, the delivery needle 330 is configured to be inserted within the body before the dilator 100. The method of inserting the dilator 100 via the delivery needle 330, as disclosed below, is herein referred to as the "pull" method. The delivery needle 330 includes a handle 331 and a needle 332 with a tip 333. The needle 332, which has a C-shaped curvature, is coupled to the handle 331. The needle 332 can have any suitable shape and/or size. For example, in some embodiments, the needle 332 can have the same shape and/or size as the needle 232 of the delivery needle 230 shown in FIG. 2.

When the delivery needle 330 is coupled to the dilator 100, the tip 333 of the needle 332 is disposed within, or adjacent to, the distal opening 107 defined by the dilator 100. More specifically, as shown in FIG. 3, the tip 333 of the needle 332 extends within the lumen of the dilator 100. In some embodiments, the tip 333 and/or another portion of the needle 332 can form an interference fit with the dilator 100 when the needle 332 is disposed within the distal opening 107. In this manner, the dilator 100 can be restricted from moving or uncoupling from the delivery needle 330 during insertion. In some embodiments, the tip 333 and/or another portion of the needle 332 can define a groove or recess configured to receive and/or couple to the distal end portion 102 of the dilator 100.

In use, the delivery needle 330 is inserted into the body via an exit incision, such as, for example, a supra-pubic incision. The exit incision is the incision from which the distal end portion 102 of the dilator 100 will extend once placed, as discussed in more detail herein. In some embodiments, the exit incision can be, for example, a retro-pubic incision, a perineum incision and/or the like. The delivery needle 330, which can be operated, for example, by a surgeon, is pushed through the body tissue toward an entry point adjacent the tissue or organ to be engaged by the implant. Once the tip 333 of the needle 332 passes through the entry point and enters a region of the pelvic area where it can be accessed (e.g. via a vaginal incision), the delivery needle 330 is coupled to the dilator 100 in the manner described above. The delivery needle 330, with the dilator 100, is then retracted or pulled back into the body in the opposite direction from which it was inserted.

The delivery needle 330 continues to retract through the body, pulling the dilator 100, until the distal end portion 102 of the dilator 100 extends from the body through the supra-pubic incision. In some embodiments, pulling the delivery needle 330 through the body includes pulling the delivery needle 330 and a portion of the dilator 100 through an obturator membrane and out through a perineal incision. The delivery needle 330 can then be uncoupled from the dilator 100 and removed from the body. In some embodiments, however, the delivery needle 330 is removed from or disposed outside of the body when the delivery needle 330 is uncoupled from the dilator 100. In embodiments where a portion of the delivery needle 330 (e.g., the tip 333) is disposed within the body when the delivery needle 330 is uncoupled from the dilator 100, the delivery needle 330 can be removed by moving (or pulling) the remainder of the needle 332 from the body in the same direction along which it pulled the dilator 100 through the body. In this manner, the delivery needle 330 is removed from the supra-pubic incision the same incision through which it was inserted). The dilator 100 remains within the body.

The needles 232 and/or 332 can be constructed from any suitable material and can have any suitable shape and/or size, as discussed briefly above. Similarly, the handles 231 and/or 331 can be any suitable handle. The needles 232 and/or 332 can be constructed of any suitable material and can have any suitable shape and/or size.

In some embodiments, the needle (e.g., needle 232 and/or needle 233) can include a coupling member (not illustrated) configured to couple the needle to the dilator 100. The coupling member, which can be disposed on the distal end of the needle, is configured to be disposed within the lumen of the dilator 100 when the needle is coupled to the dilator 100. In some embodiments, the coupling member can be portion of the needle having an increased diameter such that the needle is coupled to the dilator 100 via friction. Said another way, the dilator 100 and the needle can form an interference fit via the coupling member, when the coupling member is disposed within the lumen of the dilator 100. In some such embodiments, the coupling member can be remotely controlled such that the diameter of that portion of the needle can increase and/or decrease on command. The coupling member can be actuated, for example, by pulling a wire on a handle (e.g., handle 231 and/or 331) of the needle, by pushing a button disposed on the handle, by squeezing a portion of the handle, and/or the like.

In some embodiments, the coupling member can include female threads configured to receive male threads disposed on the distal end portion 102 of the dilator 100. In this manner, the needle (e.g., needle 232 and/or needle 233) and the dilator 100 are releasably and threadedly coupled together.

Figure 4:
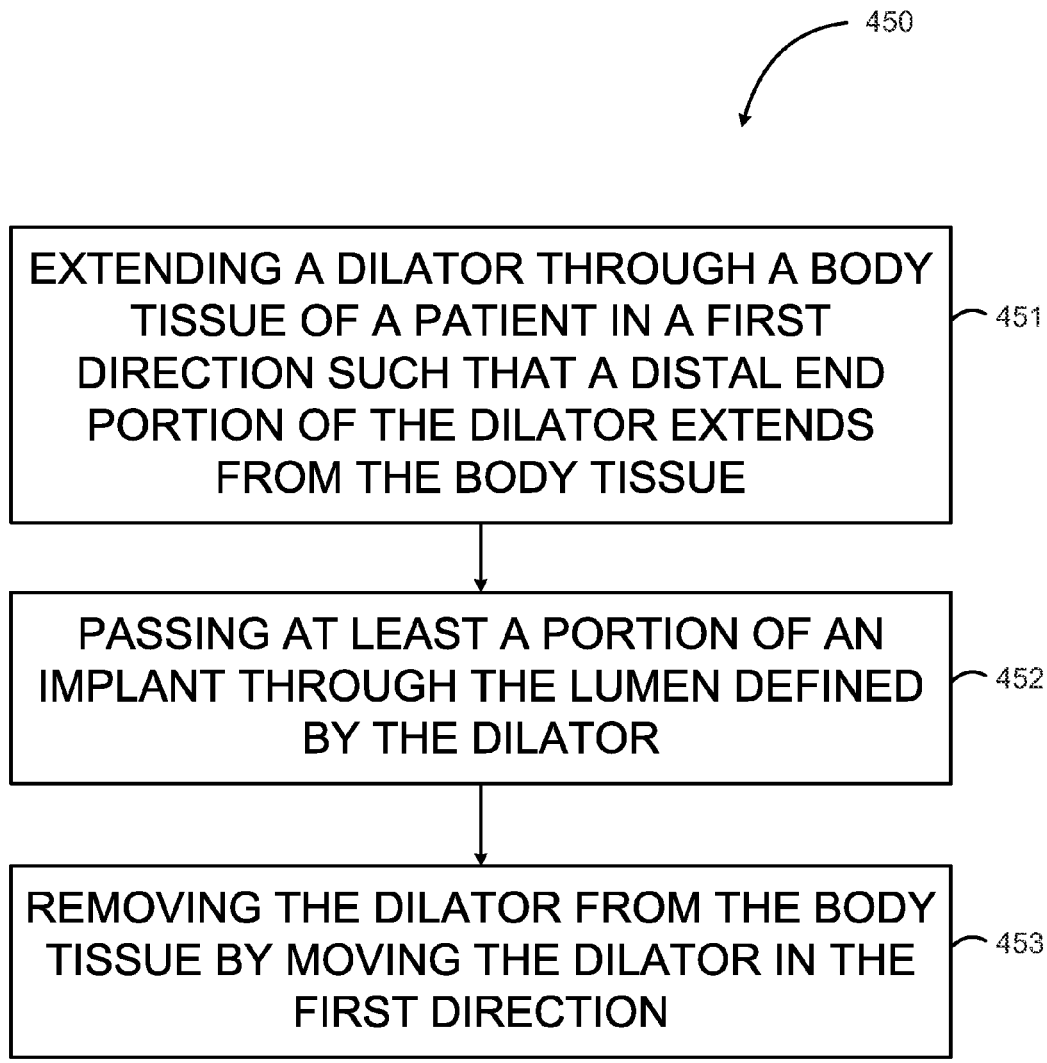
FIG. 4 is a flow chart of a method of inserting an implant into a body using the dilator in FIG. 1 according to an embodiment.
Figure 5:
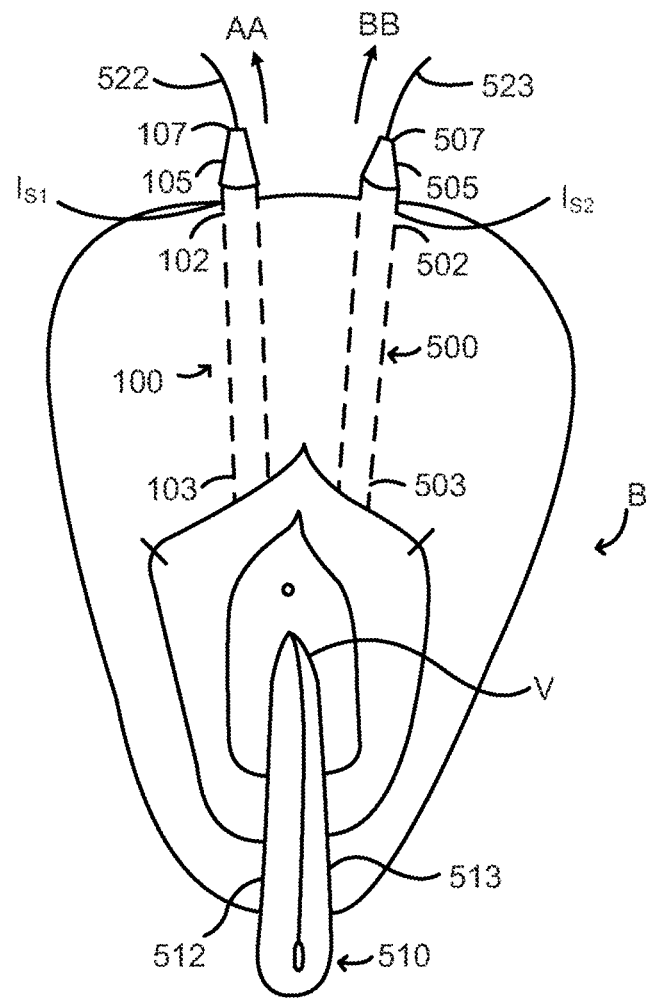
FIGS. 5-8 are schematic illustrations showing a method of inserting the implant into the body using the dilator in FIG. 1.
Figure 6:
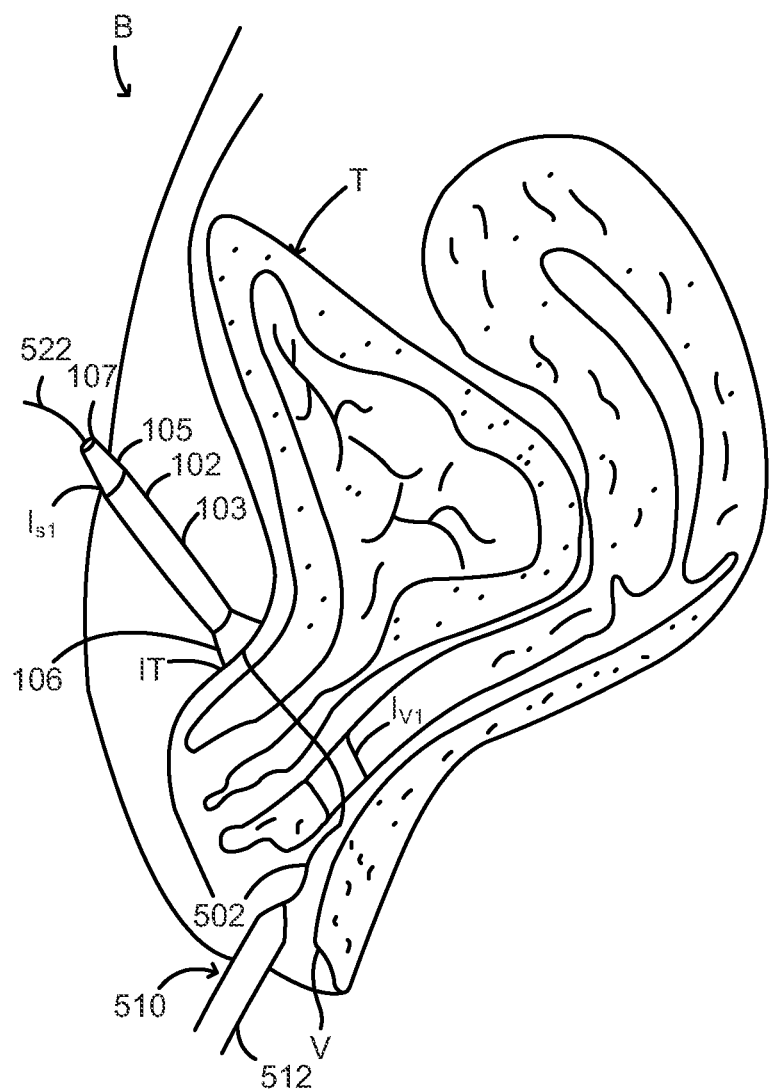

FIG. 4 is a flow chart of a method 450 of inserting an implant 510 into a body B of a patient. The method illustrated in FIG. 4 is discussed with references FIGS. 5-8, which are schematic illustrations of the implant 510 being inserted into the body B via dilators 100 and 500. The term "implant" will be referred to herein as a "sling," unless otherwise specified. It should be understood, however, that the implant 510 can be any suitable implant including, but not limited to, a sling. For example, the implant 510 can be a mesh tape having a flat configuration or a rolled configuration. The method 450 includes extending a dilator through a body tissue of a patient in a first direction such that a distal end portion of the dilator extends from the body tissue, 451. Referring to FIGS. 5 and 6, the dilator 100 extends through the body B of the patient in a distal direction AA such that the distal end portion 102 of the dilator 100 extends from the body B. Similarly, the dilator 500 extends through the body B of the patient in a distal direction BB such that a distal end portion 502 of the dilator 500 extends from the body B. The dilator 500 has substantially the same structure and operation as dilator 100 and thus, will not be described in detail herein. Also, it should be understood that, during the procedures described herein, the dilator 500 performs the same steps or operations that dilator 100 performs. Therefore, when the dilator 100 is described as or referred to in performing a particular step or operation, it should be understood that dilator 500 is also involved in or performing that particular step or operation, unless otherwise specified.

The dilator 100 is inserted into the body B of the patient via a vaginal incision, $I_V$ (shown in FIG. 6). The dilator 500 is also inserted into the body B of the patient via the vaginal incision $I_V$. In this manner, there is only a single incision in the vaginal wall V through which both dilators 100 and 500 are inserted to access the tissue through which they will extend to the exterior of the body B, i.e. through incisions in the skin of body B. The incision $I_V$ can be made at any suitable location along the vaginal wall V depending on the intended implantation site of the sling 510 within the pelvic region. For example, the vaginal incision $I_V$ is shown in FIG. 6 as being located in the anterior vaginal wall V proximate the mid-urethra (i.e., the intended implantation location/site).

The distal end portion 102 of the dilator 100 extends from the body B of the patient via a first supra-pubic incision $I_{S1}$. Similarly, the distal end portion 502 of the dilator 500 extends from the body B of the patient via a second suprapubic incision $I_{S2}$. The first supra-pubic incision $I_{S1}$ is located toward the right side of the body B and the second supra-pubic incision $I_{S2}$ is located toward the left side of the body B relative to the perspective of the patient. In some embodiments, however, the supra-pubic incisions $I_{S1}$ and $I_{S2}$ can be made at any location in the supra-pubic region of the body B. In some embodiments, the location of the supra-pubic incisions $I_{S1}$ and/or $I_{S2}$ can depend, for example, on the intended implantation site of the sling 510 within the pelvic region.

The dilator 100 can be inserted into the body B using one of the methods described above with reference to FIGS. 2 and 3. More particularly, the dilator 100 can be pushed into the body B (through body tissue) using, for example, the delivery needle 230 (i.e., the "push" method). Or, the dilator 100 can be pulled into the body B using, for example, the delivery needle 330 the "pull" method), in most instances, however, the "push" method is regularly used for procedures involving supra-pubic incisions. As such, the dilator 100 is inserted into the body B by being pushed through the vaginal incision $I_V$ and further through the pelvic region (including, the tissue in the supra-pubic space), in distal direction AA, until the distal end portion 102 of the dilator 100 extends from the first supra-pubic incision $I_{S1}$. In some embodiments, the dilator 100 can be inserted into the body B in a manner different from the dilator 500. For example, the dilator 100 can be inserted into the body B via the "push" method, and the dilator 500 can be inserted into the body B via the "pull" method. Regardless of the method used to insert the dilators 100 or 500, the dilator 100 is moved through the body B in direction AA during insertion and dilator 500 is moved through the body B in direction BB during insertion.

When the dilator 100 is extended through the body B, as shown in FIGS. 5 and 6, the proximal end portion 103 of the dilator 100 is disposed within at least the first layer of tissue $T_1$ (via a first tissue layer incision $I_T$) in which the sling 510 is to be anchored and a proximal-most end (not identified) of the dilator 100 is flush with that first layer of tissue $T_1$. In some embodiments, however, the proximal-most end of the dilator 100 can be flush with the vaginal wall V (i.e., the vaginal tissue). The placement of the proximal-most end of the dilator 100 can facilitate a more accurate placement of the sling 510 at the desired implantation site within the body B. For example, the ability to tension and/or adjust the sling 510 with respect to the urethra (or another desired implantation site) may be restricted in instances where the proximal-most end(s) of the dilators 100 and/or 500 extend beyond the first layer of tissue $T_1$. In instances where the proximal-most end(s) of the dilators 100 and/or 500 are recessed within that first layer of tissue $T_1$, the tissue surrounding the first tissue layer incision $I_T$ can close up around the dilator 100. In some embodiments, however, the proximal-most end of the dilator 100 can be recessed within the first layer of tissue $T_1$ or can extend into the vagina through the vaginal incision h.

As shown in FIG. 5, a first suture 522 is disposed within the lumen defined by the dilator 100. The first suture 522 has a first portion (not identified), which extends from the distal opening 107 of the dilator 100, and a second portion (not identified), which is coupled to a first arm 512 of the sling 510. Similarly, a second suture 523 is disposed within the lumen defined by the dilator 500. The second suture 523 has a first portion (not identified), which extends through the distal opening 507 of the dilator 500, and a second portion (not identified), which is coupled to a second arm 513 of the sling 510. As discussed in more detail herein, the sutures 522 and 523 are configured to facilitate the placement of the sling 510 within the body B. During this phase of the implantation procedure, however, the sling 510 may remain outside of the body B.

Figure 7:
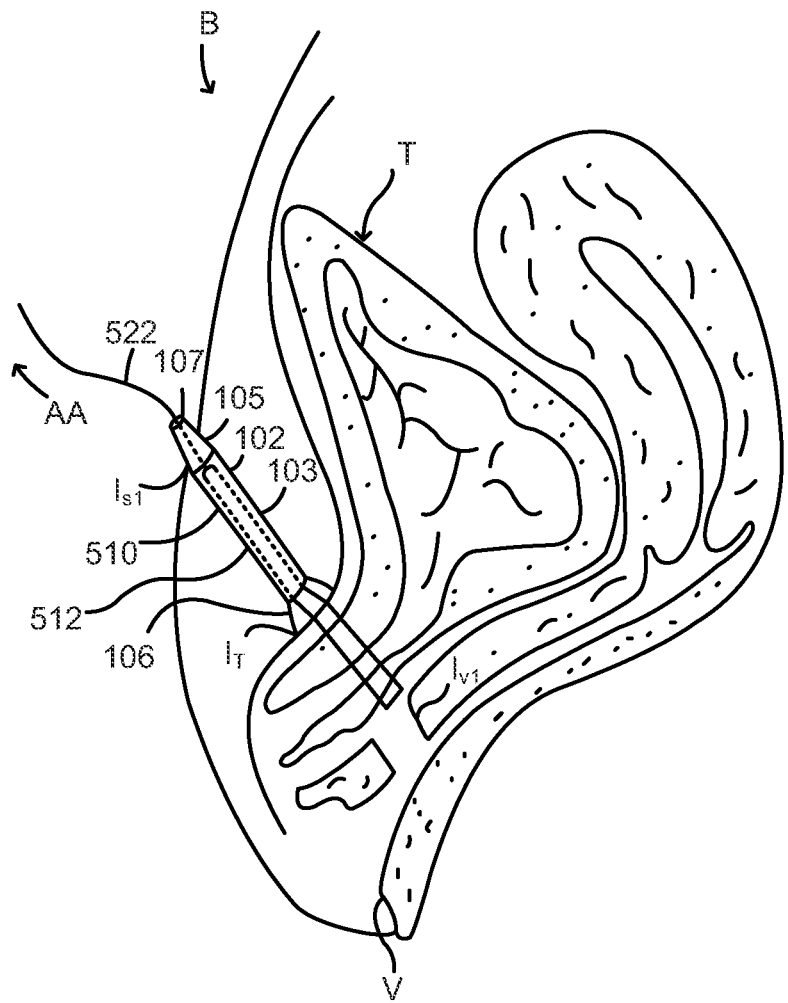

Returning to the flow chart shown in FIG. 4, at least a portion of an implant can be passed through the lumen defined by the dilator, 452. As shown in FIG. 7, the first arm 512 of the sling 510 is passed or moved in distal direction AA through the lumen defined by the dilator 100. More specifically, the first portion of the first suture 522 is moved in distal direction AA (i.e., away from the body B and/or the dilator 100) such that the first arm 512 of the sling 510 is moved in the distal direction AA. The first suture 522 can continue to be moved or pulled in the distal direction AA until the first arm 512 of the sling 510 is in the desired position within the lumen defined by the dilator 100. The desired position of the first arm 512 of the sling 510 within the lumen can, for example, correspond to the desired location of the sling 510 within the body B after implantation. Such a desired position can be achieved by, for example, adjusting and/or tensioning the first arm 512 of the sling 510 within the lumen relative to the second arm 513. The first suture 522 is, therefore, configured to guide the first arm 512 of the sling 510 into the lumen defined by the dilator 100 and to facilitate its placement within the lumen.

As shown in FIG. 7, the dilator 100 is configured to act a barrier between the first arm 512 of the sling 510 and the body B (including the body tissue through which the dilator is passed) when the first arm 512 is disposed within the lumen of the dilator 100. Said another way, the dilator 100 substantially prevents the first arm 512 of the sling 510 from contacting body tissue (other than the organ it is intended to support) when the first arm 512 is disposed within the lumen of the dilator 100. The first arm 512 of the sling 510 has a length sufficient to extend through body tissue from the vaginal incision $I_V$ or the desired implantation site, to the first supra-pubic incision $I_{S1}$. The length of the first arm 512 of the sling 510, however, is shorter than the length of the dilator 100. As a result, the first arm 512 of the sling 510 remains within the lumen of the dilator 100 while at least the first portion of the suture 522 extends through the distal opening 107 of the dilator 100 and outside of the body B. In some embodiments, however, the first arm 512 of the sling 510 can have any suitable length. For example, in some embodiments, the length of the first arm 512 of the sling 510 can be greater than the length of the dilator 100 such that a portion of the first arm 512 can extend through the distal opening 107 of dilator and/or outside of the body B.

Figure 8:
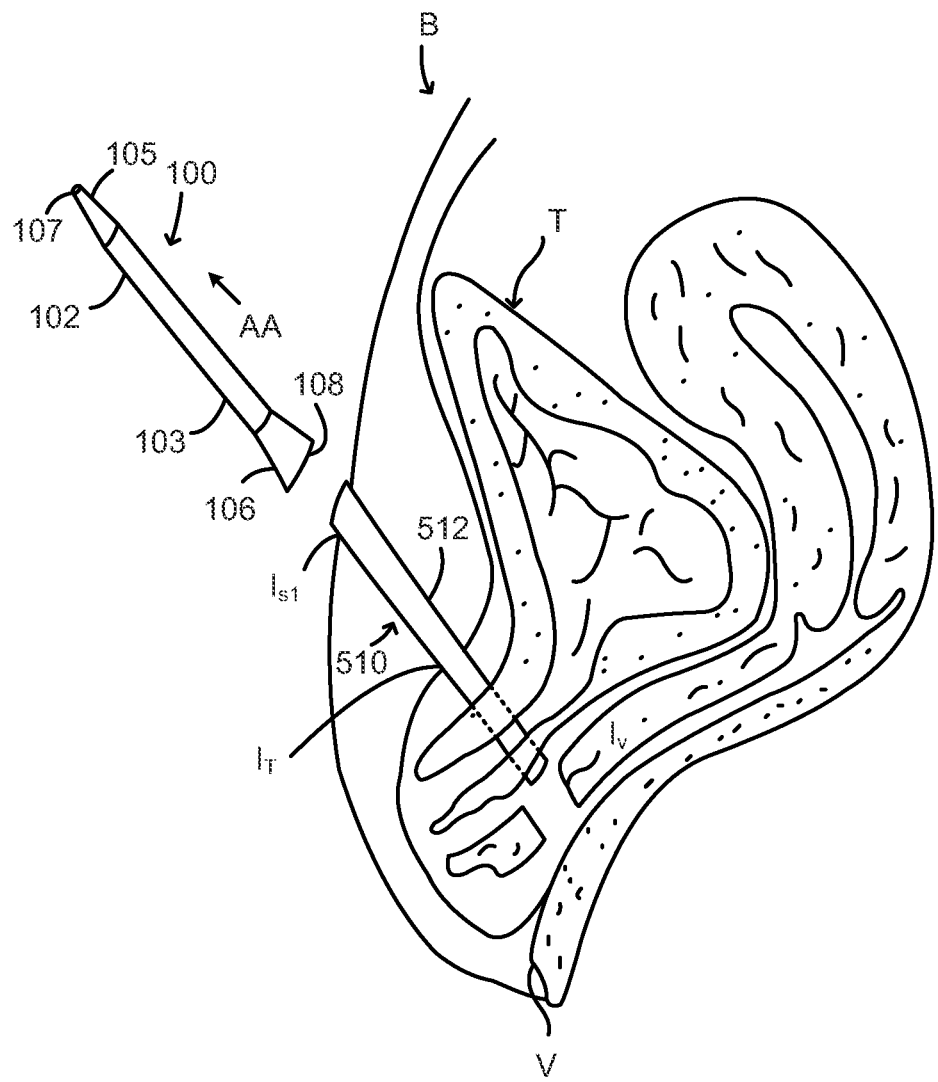

Returning to the flow chart shown in FIG. 4, the dilator is removed from the body tissue by moving the dilator in the first direction, 453. As shown in FIG. 8, the dilator 100 is removed from the body B by moving the dilator 100 in the distal direction AA. In this manner, the dilator 100 is inserted into the body B and removed from the body B in the same direction. Thus, the dilator 100 enters the body B via the vaginal incision $I_V$ and exits the body B via the first supra-pubic incision $I_{S1}$.

As shown in FIG. 8, the sling 510 remains within the body B after the dilator 100 is removed from the body B. Thus, the sling 510 is in contact with the body tissue between the first supra-pubic incision $I_{S1}$ and the first layer tissue incision $I_T$ after the dilator 100 is removed from the body B. In some embodiments, the sling 510 can be configured to promote tissue ingrowth in the surrounding bodily tissue (e.g., the tissue between the first supra-pubic incision and the first layer tissue incision $I_T$ and/or the tissue of the organ) alter the dilator 100 is removed and the sling 510 is placed in contact with the tissue of body B.

The sling 510 maintains a substantially constant position within the body B when the dilator 100 is removed.

Once the dilator 100 is removed from the body B, the sutures 522 and/or 523 can be trimmed off or otherwise removed from the respective arms 512 and/or 513 of the sling 510. The sling 510 itself can also be trimmed after the dilator 100 is removed form the body B. Additionally, the vaginal incision $I_V$, the first tissue layer incision $I_T$ (or any other internal incisions), and/or each of the supra-pubic incisions $I_{S1}$ and $I_{S2}$ can be closed via any suitable manner.

Although the sling 510 is illustrated and described above as being coupled to sutures 522 and 523, in other embodiments, the sling 510 is not coupled to sutures. In such embodiments, the first arm 512 of the sling 510 can be passed through the lumen defined by the dilator 100 via, a pusher or like device. Similarly, the second arm 513 of the sling 510 can be passed through the lumen defined by the dilator 500 via a pusher or like device. In some embodiments, the sling 510 is attached to only one of the sutures 522 or 523.

Figure 9:
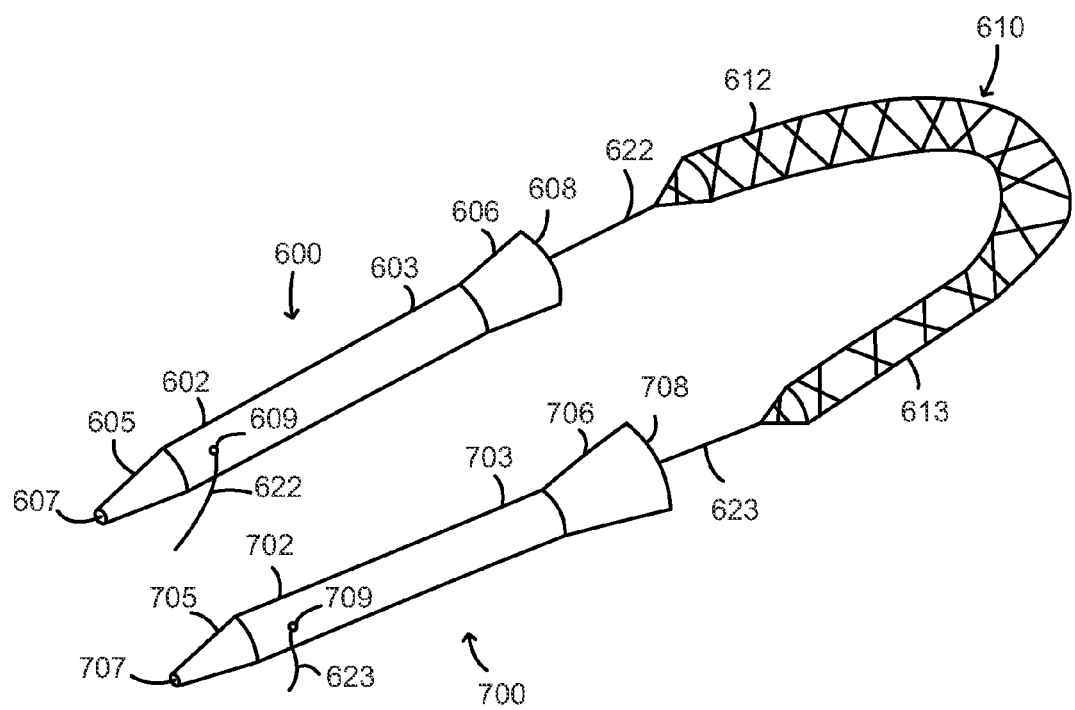
FIG. 9 is a schematic illustration of a dilator assembly according to an embodiment.

FIG. 9 is a schematic illustration of a dilator assembly, which includes dilators 600 and 700 coupled to an implant 610. The dilators 600 and 700 are configured to be inserted within a body of a patient and to deliver the implant 610 within the body. The term "implant" will be referred to herein as a "sling" in the same manner discussed above with reference to implant 510 (i.e., sling 510). The dilator 600 includes a proximal end portion 603 having an enlarged portion 606, and a distal end portion 602 having a tapered tip 605. Additionally, the dilator 600 defines a distal opening 607, a proximal opening 608, an aperture 609 and a lumen (not identified) extending therethrough. The dilator 600 has substantially the same structure and operation as dilator 100, but includes an aperture 609 in the distal end portion 602 of the dilator 600. Thus, the proximal end portion 603, the distal end portion 602, the enlarged portion 606, and the tapered tip 605 have substantially the same structure and operation as the proximal end portion 103, the distal end portion 102, the enlarged portion 106, and the tapered tip 105 of the dilator 100, and are, therefore, not described in detail herein unless otherwise specified. Additionally, the distal opening 607, the proximal opening 608, and the lumen have substantially the same structure and operation as the distal opening 107, the proximal opening 108, and the lumen defined by the dilator 100, and are, therefore, not described in detail herein unless otherwise specified. Furthermore, the dilator 700 has substantially the same structure and operation as dilator 600 and thus, will not be described in detail herein unless otherwise specified.

The aperture 609 is located in the distal end portion 602 of the dilator 600. The aperture 609 is configured to receive a portion of a first suture 622, as described in more detail herein. The aperture 609 can have any suitable shape and/or size. For example, although the aperture 609 is illustrated in FIG. 9 as having a substantially circular shape, in other embodiments, the aperture 609 can have, for example, an oval shape, a square shape, a star shape and/or the like. Additionally, the aperture 609 can be formed by any suitable process, such as, for example, molding, drilling, casting, or the like.

The sling 610 is operatively coupled to the dilators 600 and 700 via sutures 622 and 623, respectively. The sling 610 is configured to be implanted within the body to support a desired tissue or organ within the body. The sling 610, which is illustrated in FIG. 9 as a flat mesh tape, includes a first arm 612 and a second arm 613. The first arm 612 is coupled to a second portion (not identified) of the first suture 622, and the second arm 613 is coupled to a second portion (not identified) of the second suture 623. As will be described in more detail herein, the first arm 612 is configured to be implanted within the body via the dilator 600 and the second arm 613 is configured to be implanted within the body via the dilator 700. The arms 612 and 613 are configured to be received within the lumens of the dilators 600 and 700, respectively.

As shown in FIG. 9, the first suture 622 is disposed within at least a portion of the lumen defined by the dilator 600 when the second portion of the first suture 622 is coupled to the first arm 612 of the sling 610. The first suture 622 includes a first portion (not identified) that extends through the aperture 609 (i.e., from the inside-out) and is coupled to the distal end portion 602 of the dilator 600 via the aperture 609. In some embodiments, the first portion of the first suture 622 can include a knot to prevent the first portion from receding back through the aperture 609, which thereby couples the first suture 622 to the dilator 600. The first portion of the first suture 622, however, can include any suitable anchor to prevent the first portion from receding back through the aperture 609. For example, in some embodiments, the first portion of the first suture 622 can be fixedly coupled within the aperture 609 via an adhesive.

The first portion of the first suture 622 can be coupled to the distal end portion 602 of the dilator 600 via the aperture 609 in any suitable manner. For example, in some embodiments, the first portion of the first suture 622 can be pulled through the distal opening 607 of the dilator 600 and then laced through the aperture 609 from the outside-in. A knot can be formed at the first portion of the first suture 622 to prevent the first suture 622 from receding back through the aperture 609. In some embodiments, a portion of the exposed first suture 622 can further be formed into a loop (shown, for example, in FIGS. 11 and 12). The surgeon, for example, can exert a force on the first suture 622 via the loop such that the knot (or other anchor) is forced through the aperture 609, thereby uncoupling the first suture 622 from the dilator 600. The loop can then be used to pull or move the first arm 612 of the sling 610 into the lumen of the dilator 600, as described herein.

In some embodiments, a kit can include the dilators 600 and 700 and the implant 610. In some such embodiments, the kit can be pre-assembled such that the implant 610 is coupled to the dilators 600 and 700 via sutures 622 and 623, respectively. The implant 610 can be coupled to the dilators 600 and/or 700 in any manner described herein. In some embodiments, the sling 610 can be pre-formed into a roll and included in the kit. In this manner, the sting 610 can be inserted into the body in its pre-formed configuration and can, for example, unroll into its original configuration at some time during or after the implantation procedure.

Figure 10:
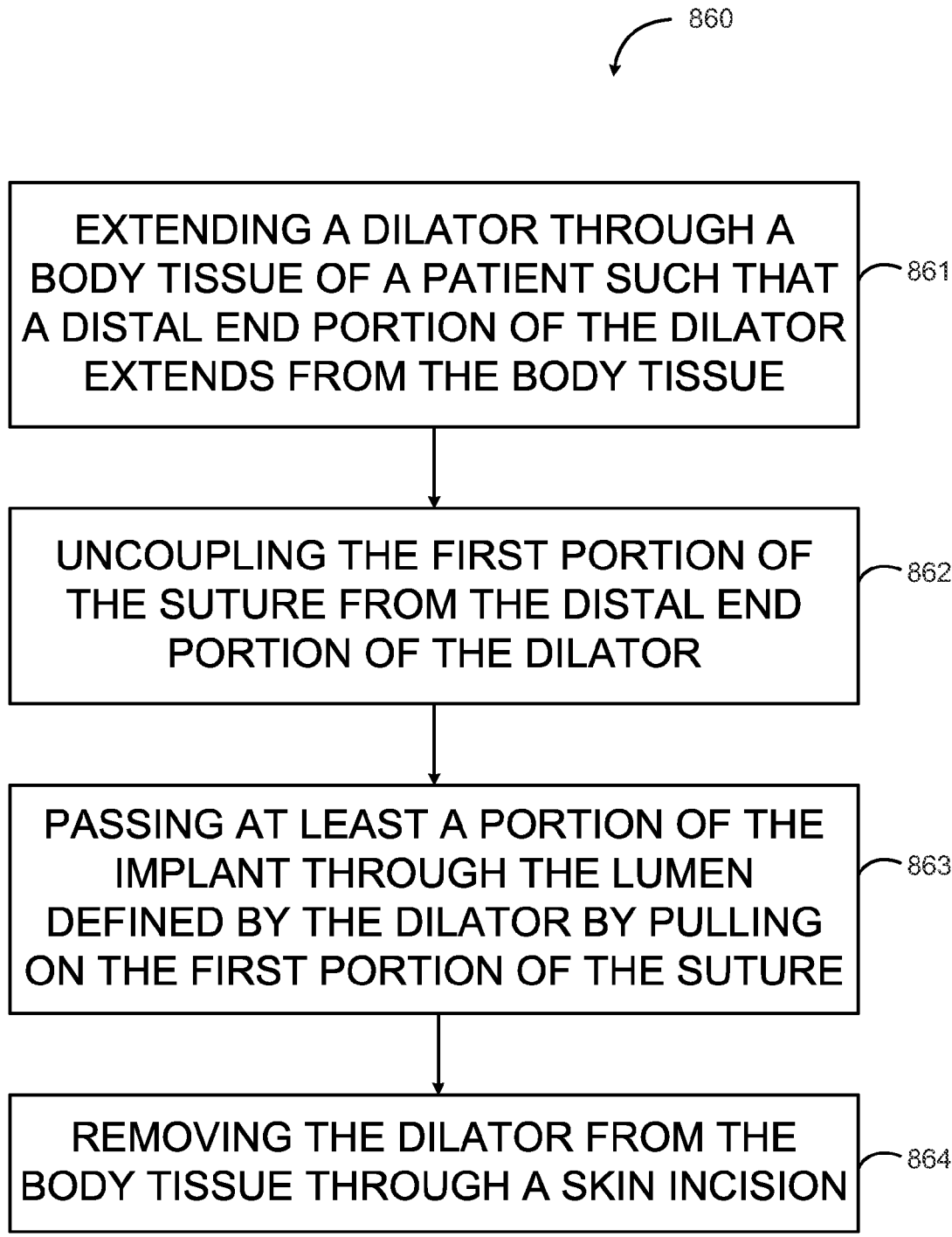
FIG. 10 is a flow chart of a method of inserting an implant into a body using the dilator assembly in FIG. 9 according to another embodiment.
Figure 11:
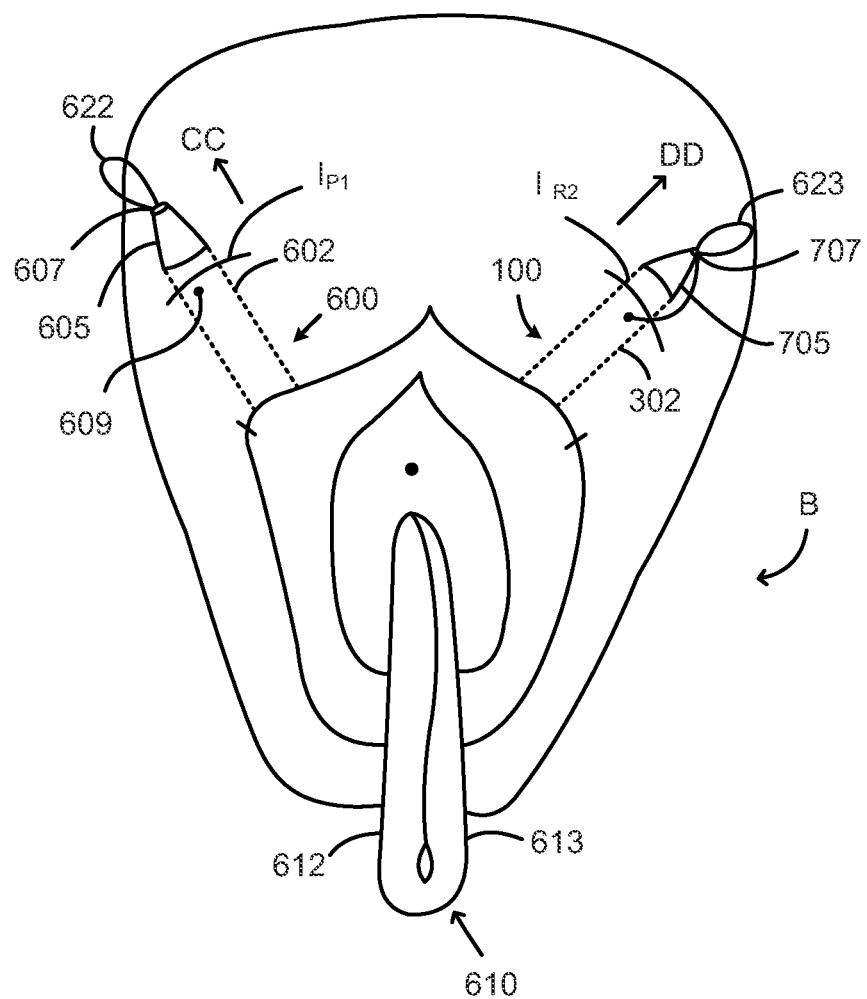
FIGS. 11-15 are schematic illustrations showing a method of inserting the implant into the body using the dilator assembly in FIG. 9.
Figure 12:
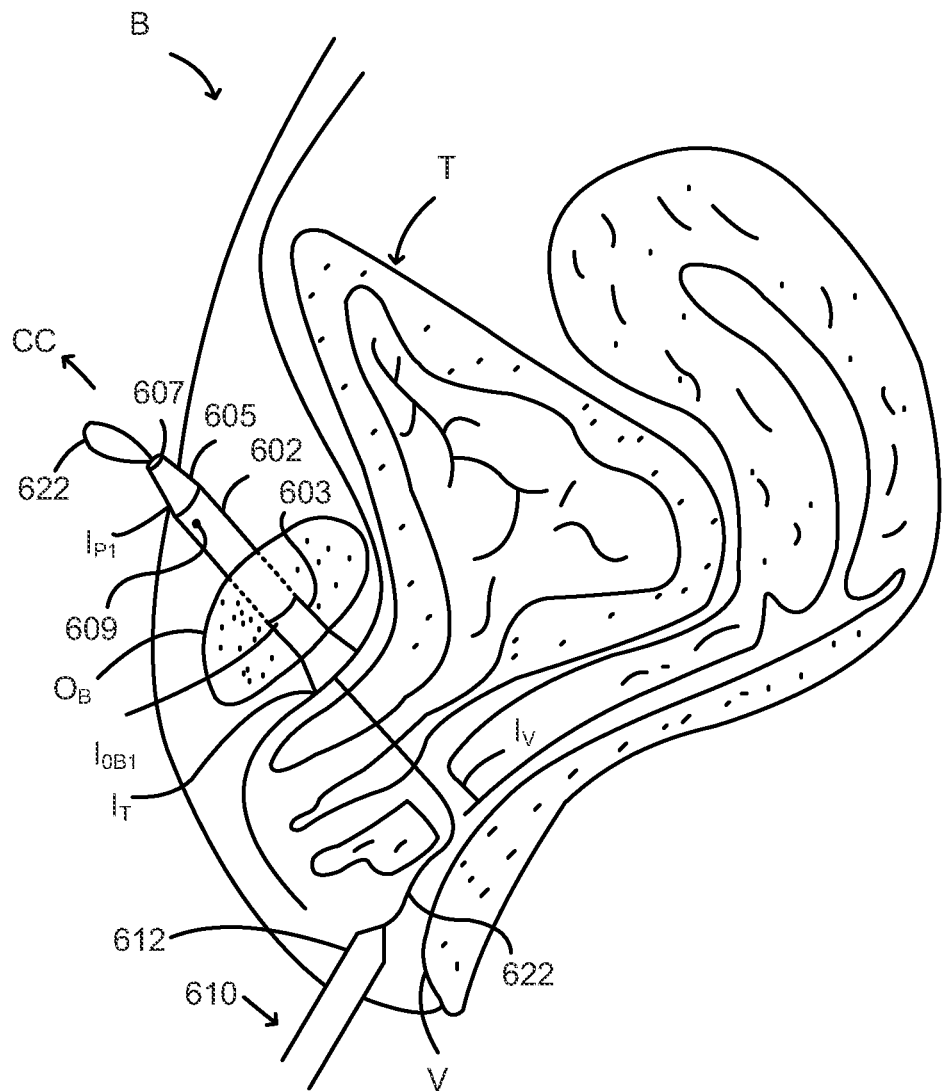

FIG. 10 is a flow chart of a method 860 of inserting an implant 610 into a body B of a patient. The method illustrated in FIG. 10 is discussed with references FIGS. 11-15, which are schematic illustrations of the implant 610 being inserted into the body B via the dilator assembly shown in FIG. 9. The term "implant" will be referred to herein as a "sling," as discussed above. The method 860 includes extending a dilator through a body tissue of a patient such that a distal end portion of the dilator extends from the body tissue, 861. Referring to FIGS. 11 and 12, the dilator 600 extends through the body B (including internal body tissue) of the patient such that the distal end portion 602 of the dilator 600 extends from the body B. Similarly, the dilator 700 extends through the body B of the patient such that a distal end portion 702 of the dilator 700 extends from the body B. It should be understood that, during the procedures described herein, the dilator 700 performs the same steps or operations that dilator 600 performs. Therefore, when the dilator 600 is described as or referred to in performing a particular step or operation, it should be understood that dilator 700 is also involved in or performing that particular step or operation, unless otherwise specified.

The dilator 600 is inserted into the body B via a vaginal incision, $I_V$ (shown in FIG. 12). The dilator 700 is also inserted into the body B via the vaginal incision $I_V$. In this manner, there is only a single incision in the vaginal wall $I_V$ through which both dilators 600 and 700 extend. In some embodiments, however, the dilators 600 and/or 700 are inserted into the body B via separate vaginal incisions. The incision $I_V$ can be made at any location along the vaginal wall V depending on the intended implantation site of the sling 610 within the pelvic region, as described above. When the dilator 600 is extended through the body B, as shown in FIG. 12, the proximal end portion 603 of the dilator 600 is disposed within at least the first layer of tissue $T_1$ (via, a first tissue layer incision $I_T$) in which the sling 510 is to be anchored and a proximal-most end (not identified) of the dilator 600 is flush with that first layer of tissue $T_1$ as described above.

As shown in FIG. 12, the dilator 600 extends through an obturator membrane $O_B$ within the body B when the distal end portion 602 of the dilator 600 extends through the body 13. More particularly, the dilator 600 extends through a first obturator incision $I_{OB1}$ when the distal end portion 602 of the dilator 600 extends from a first perineum incision $I_{P1}$. Similarly, the dilator 700 extends through the opposing obturator membrane (not illustrated) via a second obturator incision (not illustrated) when the distal end portion 702 of the dilator 700 ends from the body B via a second perineum incision $I_{P2}$. The first perineum incision $I_{P1}$ and the obturator membrane $O_B$ are located toward the right side of the body B, and the second perineum incision $I_{P2}$ and opposing obturator membrane are located toward the left side of the body B relative to the perspective of the patient. In some embodiments, however, the perineum incisions $I_{P1}$ and $I_{P2}$ can be made at any location in the perineum region of the body B. Similarly, the obturator incisions (e.g., the first obturator incision $I_{OB1}$) can be made at any location along the obturator membranes the obturator membrane $O_B$) The location of the perineum incisions $I_{P1}$ and/or $I_{P2}$ can depend, for example, on the intended implantation site of the sling 610 within the pelvic region.

The dilator 600 can be inserted into the body B using one of the methods described above with reference to FIGS. 2 and 3. More particularly, the dilator 600 can be pushed through the body B using, for example, the delivery needle 230 (i.e., the "push" method). Or, the dilator 600 can be pulled through the body B using, for example, the delivery needle 330 (i.e., the "pull" method). In most instances, however, the "pull" method is regularly used for procedures involving perineum and/or obturator incisions. As such, the delivery needle (e.g., delivery needle 330) is inserted and moved within the body B along a path that includes the first perineum incision $I_{P1}$, the first obturator incision $I_{OB1}$, the first tissue layer incision $I_T$ (and any other internal body tissue incisions) and the vaginal incision $I_V$. Once the delivery needle reaches the vaginal incision $I_V$, the distal end portion 602 of the dilator 600 can be coupled to the delivery needle, in the manner described above, and inserted into the body B. The dilator 600 is inserted into the body B by being pulled in distal direction CC through the vaginal incision $I_V$, through the first tissue layer incision $I_T$, through the obturator incision $I_{OB1}$, and further through the first perineum incision $I_{P1}$ until the distal end portion 602 of the dilator 600 extends through the first perineum incision $I_{P1}$. In some embodiments, the dilator 700 can be inserted into the body B in a manner different from the dilator 600, as discussed above.

The dilators 600 and 700 are inserted into the body B in a similar configuration to that shown in FIG. 9. Similar to the configuration shown in FIG. 9, the sling 610 is operatively coupled to the dilators 600 and 700 via sutures 622 and 623 when the dilators 600 and 700 are inserted within the body B. The sutures 622 and 623 shown in FIGS. 11 and 12, however, are in a looped configuration. More specifically, with respect to dilator 600, the first portion of the first suture 622 extends through the lumen and out from the distal opening 607, then loops around the outside of the dilator 600 and through the aperture 609. The first portion of the first suture 622 disposed through the aperture 609 is then securely fastened to the dilator 600, for example, via a knot, as described above. A loop (not identified) is then formed with the portion of the first suture 622 disposed outside of the dilator 600. During this phase of the implantation procedure, the sling 610 remains outside of the body B.

Figure 13:
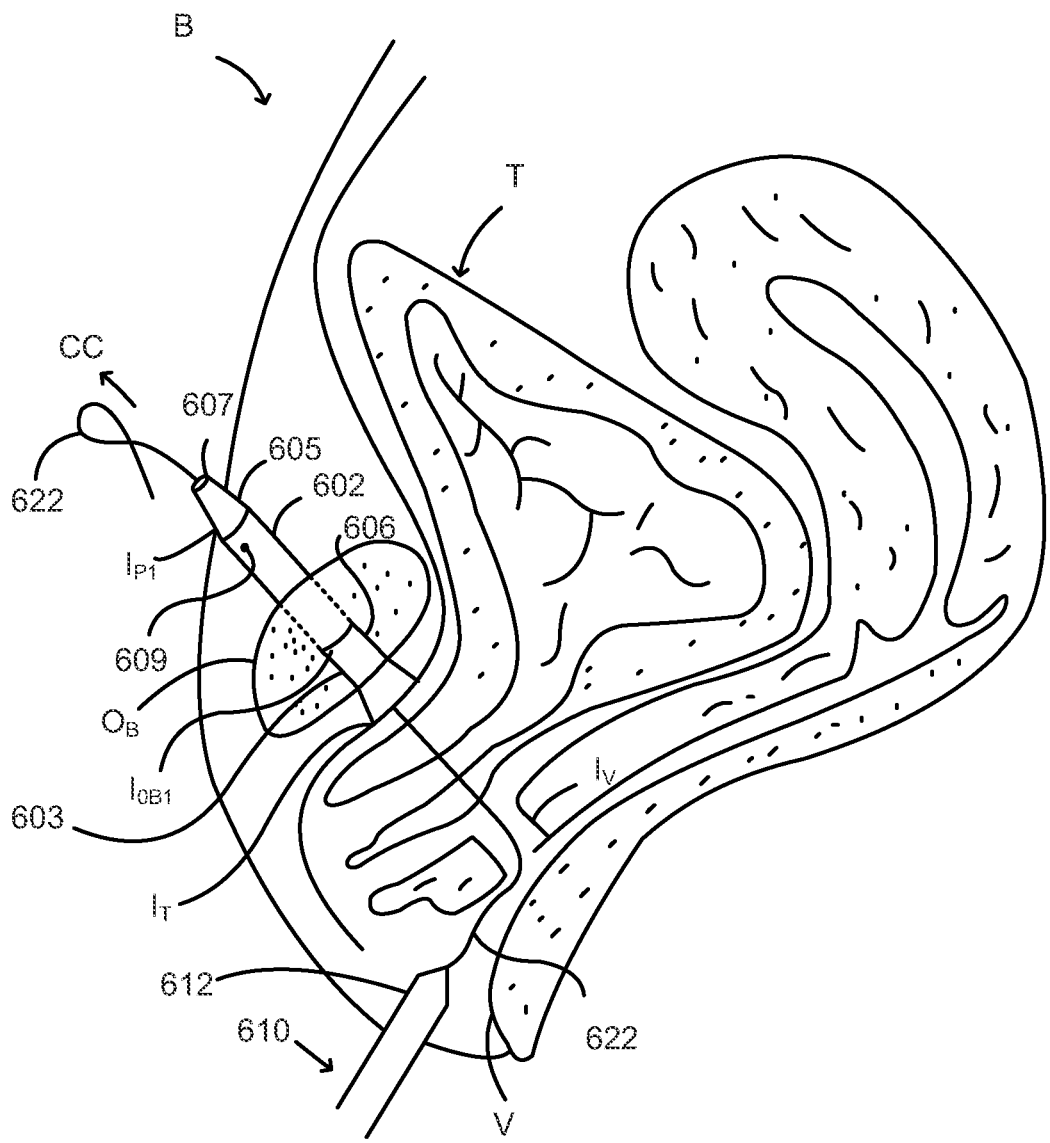

Returning to the flow chart shown in FIG. 10, the first portion of the suture is uncoupled from the distal end portion of the dilator, 862. As shown in FIG. 13, the first portion of the first suture 622 is uncoupled from the distal end portion 602 of the dilator 600 when the first suture 622 is moved in direction CC. A surgeon, for example, can pull the first suture 622 (e.g., via the loop) such that the force exerted on the first suture 622 in the distal direction CC forces the knot through the aperture 609 and, thereby uncouples the first suture 622 from the distal end portion 602 of the dilator 600. In some embodiments, however, the first portion of the first suture 622 is uncoupled from distal end portion 602 of the dilator 600 in any suitable manner, such as, for example, via severing.

Figure 14:
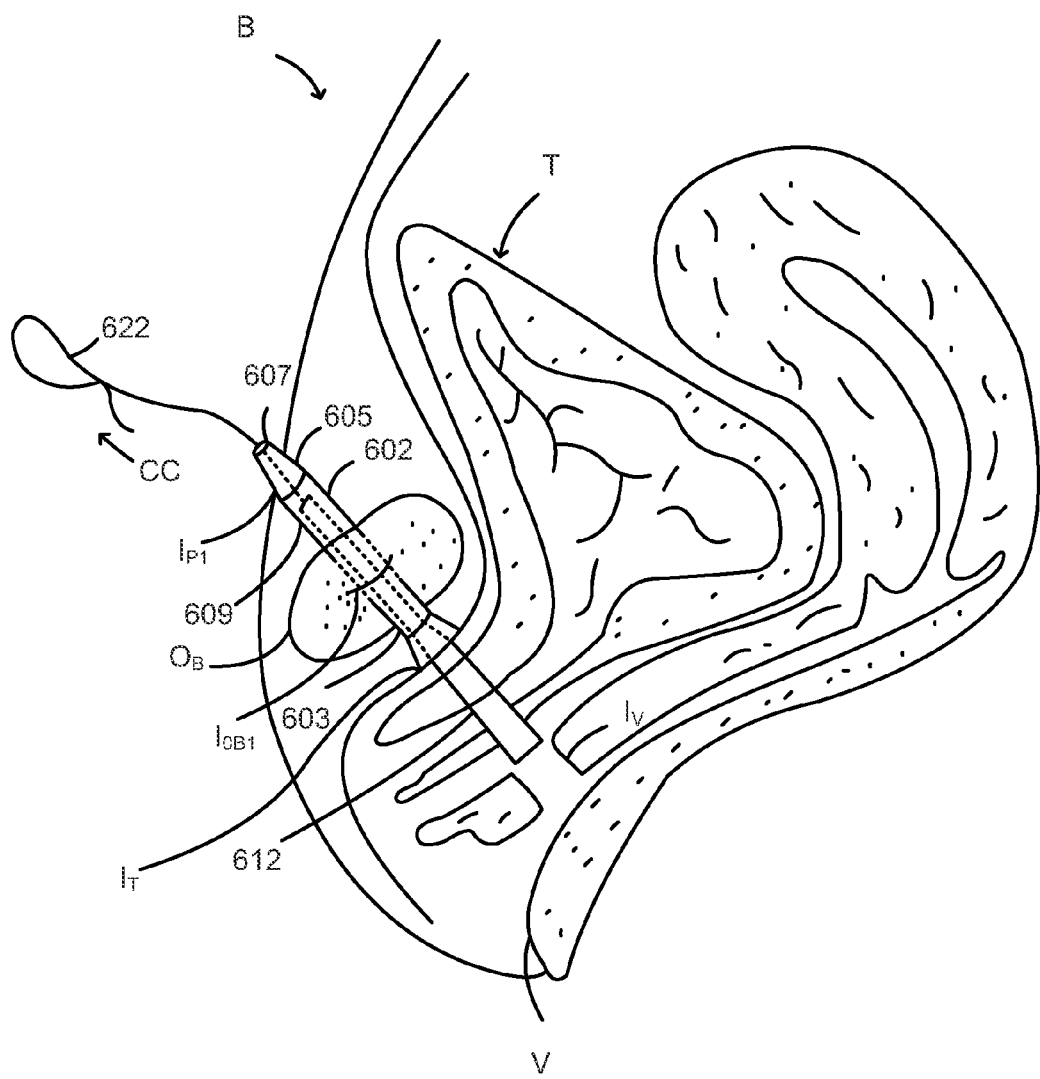

Returning to the flow chart shown in FIG. 10, at least a portion of an implant is passed through the lumen defined by the dilator by pulling on the first portion of the suture, 863. As shown in FIG. 14, the first arm 612 of the sling 610 is passed or moved through the lumen defined by the dilator 600 by pulling the first portion of the first suture 622 in distal direction CC. For example, once the first suture 622 is uncoupled from the distal end portion 602 of the dilator 600, the surgeon, for example, can continue to pull the first suture 622 (e.g., via the loop) in the distal direction CC until the first arm 612 of the sling 610 is pulled into the lumen of the dilator 600. In some embodiments, the acts of pulling the first portion of the first suture 622 to uncouple it from the dilator 600 and to pull the sling 610 into the dilator 600 is performed in a continuous motion. In some embodiments, the first suture 622 can continue to be pulled until the first arm 612 of the sling 610 is in the desired position within the lumen defined by the dilator 600. As described above, the desired position of the first aim 612 of the sling 610 within the lumen can, for example, correspond to the desired location of the sling 610 within the body B after implantation. Such a desired position can be achieved by, for example, adjusting and/or tensioning the first arm 612 of the sling 610 within the lumen relative to the second arm 613.

As shown in FIG. 14 and described above, when the first arm 612 is disposed within the lumen of the dilator 600, the dilator 600 is configured to act a barrier between the first arm 612 of the sling 610, the obturator membrane $O_B$ and the body B (including any bodily tissue other that the tissue or organ it is intended to support). The first arm 612 of the sting 610 has a length sufficient to extend through body tissue from the vaginal incision $I_V$ or the desired implantation site, to the first perineum incision $I_{P1}$. The length of the first arm 612 of the sling 610, however, is shorter than the length of the dilator 600. As a result, the first arm 612 of the sling 610 remains within the lumen of the dilator 600 while at least the first portion of the first suture 622 extends through the distal opening 607 of the dilator 600 and outside of the body B, as described above. In some embodiments, however, the first aim 612 of the sling 610 can have any suitable length, as described above. For example, in some embodiments, the length of the first arm 612 is only sufficient to extend from the vaginal incision $I_V$ or the desired implantation site, to the first obturator incision $I_{OB1}$.

Figure 15:
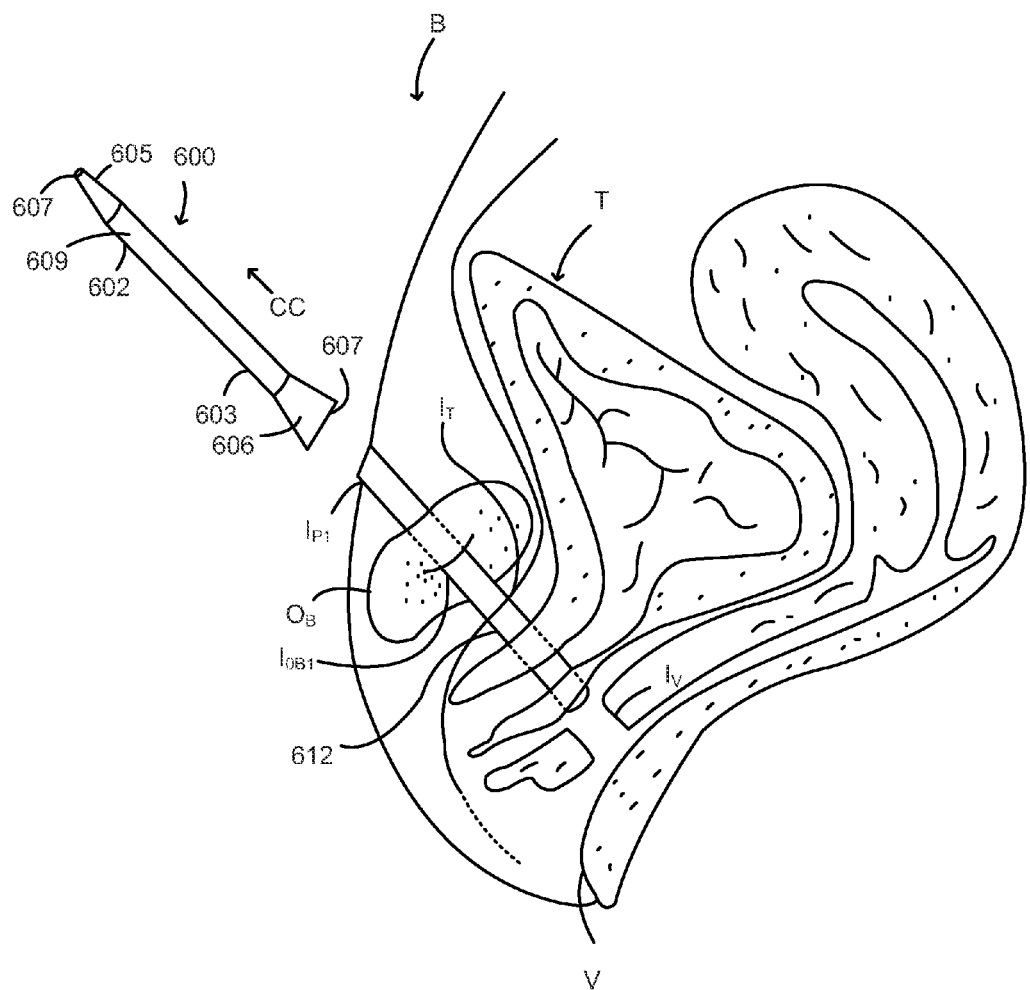

Returning to the flow chart shown in FIG. 10, the dilator is removed from the body tissue through a skin incision, 864. As shown in FIG. 15, the dilator 600 is removed from the body B through the first perineum incision $I_{P1}$. In this manner, the dilator 600 is inserted into the body B and removed from the body B in the same direction (i.e., distal direction CC). Thus, the dilator 600 enters the body B via, the vaginal incision $I_V$ and exits the body B via the first perineum incision $I_{P1}$. In some embodiments, however, the dilator 600 can be removed from the body B through the vaginal incision $I_V$. In this manner, the dilator 600 is inserted and removed from the same incision.

As shown in FIG. 15, the sting 610 remains within the body B after the dilator 600 is removed from the body B, as described above. Thus, the sling 610 is in contact with the body tissue between the first layer tissue incision $I_T$ and the first perineum incision $I_{P1}$ (including the obturator membrane $O_B$) after the dilator 600 is removed from the body B. In some embodiments, the sting 610 can be configured to promote tissue ingrowth in the surrounding bodily tissue, including the obturator membrane $O_B$, after the dilator 600 is removed and the sling 610 is placed in contact with the body B.

Once the dilators 600 and 700 are removed from the body B, the sutures 622 and/or 623 can be trimmed off or otherwise removed from the respective arms 612 and/or 613 of the sting 610. The sling 610 itself can also be trimmed off after the dilators 600 and 700 are removed form the body B. Additionally, the vaginal incision $I_V$, the first layer tissue incision $I_T$, the obturator incision $I_{OB1}$ and/or each of the perineum incisions $I_{P1}$ and $I_{P2}$ can be closed via any suitable manner.

Although the sling 610 is illustrated and described above as being coupled to sutures 622 and 623, in other embodiments, the sling 610 is not coupled to sutures. In such embodiments, the first arm 612 of the sling 610 can be passed through the lumen defined by the dilator 600 via a pusher or like device. Similarly, the second arm 613 of the sling 610 can be passed through the lumen defined by the dilator 600 via a pusher or like device. In some embodiments, the sling 610 is attached to only one of the sutures 622 or 623.

While various embodiments of the invention have been described above, it should be understood that they have been presented by way of example only, and not limitation. Thus, the breadth and scope of the invention should not be limited by any of the above-described embodiments, but should be defined only in accordance with the following claims and their equivalents. While the invention has been particularly shown and described with reference to specific embodiments thereof, it will be understood that various changes in form and details may be made.

Although the dilators illustrated and described above were used to delivery or implant an implant into a pelvic region via a specific approach, in other embodiments, the dilator(s) can be used to deliver or implant an implant into a pelvic region using a variety of different approaches, including for example, a transvaginal approach, a retropubic approach, a supra pubic approach, or a transobturator approach.

Although the dilators are illustrated and described above as being positioned within the body such that the proximal end portion of the dilators are disposed within the vaginal area and the distal end portion of the dilators are disposed adjacent the outer surface of the body, in other embodiments, a dilator is positioned within the body in the opposite configuration. For example, the dilator can be positioned within the body such that the distal end portion of the dilator is disposed within the vaginal area and the proximal end portion of the dilator is disposed adjacent the outer surface of the body. In some such embodiments, a suture coupled to an implant, or the implant itself, is pulled into the lumen of the dilator via the distal opening. In this manner, the suture and/or the implant moves or passes through the lumen of the dilator in the opposite direction to that described above (i.e., from the distal end portion of the lumen to the proximal end portion of the lumen). The suture and/or the implant can be moved through the lumen by any of the means described above. For example, in some embodiments, the suture and/or the implant is coupled to a delivery needle (e.g., delivery needle 230 or 330) and pulled through the lumen.

Although the dilators and procedures are illustrated and described above with reference to a female pelvic region, it should be understood that the same dilators and/or procedures can be used in the male pelvic region without substantial modification. For example, where the female pelvic region is accessed via a vaginal incision in the aforementioned procedures, the male pelvic region can be accessed via right and left perineum incisions. In some embodiments, the female pelvic region can be accessed via perineum incisions rather than a vaginal incision in the aforementioned procedures.

The implant(s) described herein can be formed with a variety of different materials, such as biocompatible plastics and/or metals. In some embodiments, the implant is formed at least in part with a mesh material to promote tissue in-growth. An implant can also be formed fully or in part with biological or natural materials or combinations of biological and synthetic materials. An implant can be formed at least in part with, for example, the Advantage® Mesh by Boston Scientific Corporation. Alternatively, the implant can be formed with Polyform® Synthetic Mesh material by Boston Scientific Corporation.

The implant(s) can have a variety of different configurations and/or different sizes (e.g. lengths, widths), depending on the intended use for the particular implant and the intended implantation site for the implant within the pelvic region.

The previous description of the embodiments is provided to enable any person skilled in the art to make or use the invention. While the invention has been particularly shown and described with reference to embodiments thereof, it will be understood by those skilled in art that various changes in form and details may be made. For example, a dilator can include various combinations and sub-combinations of the various embodiments described herein.

In some embodiments, a method includes extending a dilator into a body tissue of a patient in a first direction such that a distal end portion of the dilator extends from the body of the patient. The dilator defines a lumen therethrough. At least a portion of the dilator is disposed within the body tissue when the distal end portion extends from the body. At least a portion of an implant is passed through the lumen defined by the dilator. The dilator is removed from the body tissue by moving the dilator in the first direction.

In some embodiments, the dilator can be extended by pushing the distal end portion of the dilator through the body tissue.

In some embodiments, the dilator can be extended by pulling the distal end portion of the dilator through the body tissue.

In some embodiments, the dilator can be extended into a portion of the body tissue in a pelvic region of the patient.

In some embodiments, the dilator can be extended such that a proximal end of the dilator is aligned with a surface of the body tissue. In this manner, the proximal end is flush with the surface.

In some embodiments, the distal end portion of the dilator can be configured to contact a portion of a delivery needle when the dilator is being extended into the body tissue.

In some embodiments, the dilator can be extended into the body tissue via a first incision, and is removed from the body via a second incision.

In some embodiments, the portion of the implant can be passed through the lumen by pushing the portion of the implant through the lumen in the first direction.

In some embodiments, the portion of the implant can be passed through the lumen by pulling the portion of the implant through the lumen in the first direction.

In some embodiments, the portion of the implant can be passed through the lumen in a second direction opposite the first direction.

In some embodiments, the first direction can be a distal direction.

In some embodiments, a proximal end portion of the dilator can include an enlarged portion, which is in fluid communication with the lumen. In some such embodiments, the enlarged portion can be configured to facilitate the passing of the portion of the implant through the lumen.

In some embodiments, the implant can be configured to be used to treat male incontinence.

In some embodiments, a method includes extending a dilator into body tissue of a patient such that a distal end portion of the dilator extends from the body of the patient. The distal end portion of the dilator is coupled to a first portion of a suture such that the first portion of the suture is disposed outside of the body when the distal end portion of the dilator extends from the body. The suture has a second portion coupled to an implant. The dilator defines a lumen therethrough. The first portion of the suture is uncoupled from the distal end portion of the dilator and at least a portion of the implant is passed through the lumen defined by the dilator by pulling on the first portion of the suture. The dilator is removed from the body tissue through a skin incision.

In some embodiments, the method can also include coupling the first portion of the suture to the distal end portion of the dilator. In some such embodiments, the distal end portion of the dilator can define an aperture through which the first portion of the suture is disposed.

In some embodiments, after the dilator is removed from the body tissue, the method can also include, trimming the portion of the implant that extends from the bodily tissue such that the suture is detached from the implant.

In some embodiments, the dilator can be extended into a body tissue in a pelvic region of the patient.

In some embodiments, the dilator can be extended into the body tissue in a first direction, and can be removed from the body tissue in a direction substantially the same as the first direction.

In some embodiments, the dilator can be extended into the body tissue in a first direction, and can be removed from the body tissue in a second direction substantially opposite the first direction.

In some embodiments, the dilator can be extended into the body tissue and through a portion of an obturator.

In some embodiments, the distal end portion of the dilator can be configured to contact a portion of a delivery needle when the dilator is being extended into the body tissue.

In some embodiments, the suture can be uncoupled by pulling on a loop formed by the first portion of the suture such that the first portion of the suture uncouples from the distal end portion of the dilator.

In some embodiments, the incision can be one of a supra-pelvic incision, a retro-pubic incision, or a perineum incision.

In some embodiments, the implant can be configured to be used to treat male incontinence.

In some embodiments, the implant can be a mesh implant.

What is claimed is:

1. A method, comprising:
    inserting a needle of a delivery needle into a lumen of a first dilator, wherein, when the needle is inserted into the lumen of the first dilator, a tip of the needle extends outside the lumen from a first opening of the first dilator;
    extending the first dilator into a body of a patient via a vaginal incision in a direction until a distal end portion of the first dilator extends from a first supra-pubic incision, the first dilator defining the first opening disposed proximate the distal end portion and a second opening disposed proximate to a proximal end portion of the first dilator, the lumen of the first dilator extending from the first opening to the second opening, at least a portion of the first dilator being disposed within the body when the distal end portion extends from the body, wherein a first suture extends through at least a portion of the lumen of the first dilator, the first suture having a first end portion coupled to an implant;
    passing, after the extending, a first portion of the implant through the vaginal incision and then into the lumen defined by the first dilator by pulling on a second end portion of the first suture;
    removing the first dilator from the body via the first supra-pubic incision by moving the first dilator in a direction that is the same as the direction used to extend the first dilator into the body of the patient while the portion of the first portion of the implant slides out of the lumen defined by the first dilator and remains in the body, wherein the removing includes removing the needle of the delivery needle from the body of the patient via the vaginal incision and removing the first dilator from the body of the patient via the first supra-pubic incision;
    extending a second dilator into the body of the patient via the vaginal incision until a distal end portion of the second dilator extends from a second supra-pubic incision,
    wherein a second suture extends through at least a portion of the lumen of the second dilator, the second suture having a first end portion coupled to a second portion of the implant, the first dilator and the second dilator extending into the body of the patient via the same vaginal incision;
    passing, after the extending, the second portion of the implant through the vaginal incision and then into the lumen defined by the second dilator.

2. The method of claim 1, wherein the extending includes pushing the distal end portion of the first dilator through the body.

3. The method of claim 1, wherein the extending includes pulling the distal end portion of the first dilator through the body.

4. The method of claim 1, wherein the extending includes extending the first dilator into a portion of the body in a pelvic region of the patient.

5. The method of claim 1, wherein the extending includes aligning the proximal end portion of the first dilator with a surface of the body such that the proximal end portion is flush with the surface.

6. The method of claim 1, wherein, during the extending, the distal end portion of the first dilator is configured to contact a portion of the delivery needle.

7. The method of claim 1, wherein the passing includes pushing the portion of the implant through the lumen of the first dilator in a direction that is the same as the direction used to extend the first dilator into the body of the patient.

8. The method of claim 1, wherein the passing includes pulling the portion of the implant through the lumen of the first dilator in a direction that is the same as the direction used to extend the first dilator into the body of the patient.

9. The method of claim 1, wherein the direction used to extend the first dilator into the body of the patient is a distal direction.

10. The method of claim 1, wherein the proximal end portion of the first dilator includes an enlarged portion in fluid communication with the lumen of the first dilator, the enlarged portion configured to facilitate the passing.

11. A method, comprising:

inserting a needle of a delivery needle into a lumen of a dilator, the delivery needle also including a handle extending the needle, the dilator defining a first opening at a distal end portion of the dilator and a second opening at a proximal end portion of the dilator such that the lumen extends from the first opening to the second opening, wherein, when the needle is inserted into the lumen of the dilator, a tip of the needle extends outside the lumen from the first opening of the dilator;

pushing the needle and the dilator into a body of a patient via a vaginal incision until the distal end portion of the dilator extends from a supra-pubic incision, the distal end portion of the dilator being coupled to a first portion of a suture such that the first portion of the suture is disposed within the body when the distal end portion of the dilator extends from the body via the supra-pubic incision, the suture having a second portion coupled to an end portion of an implant, the distal end portion of the dilator defining an aperture proximate to the first opening, the suture extending through the aperture;

uncoupling the first portion of the suture from the distal end portion of the dilator;

passing, after the extending, at least a portion of the implant through the vaginal incision and then into the lumen defined by the dilator by pulling on the first portion of the suture and moving the suture through the aperture;

removing the needle of the delivery needle from the body of the patient through the vaginal incision; and removing the dilator from the body of the patient through the supra-pubic incision.

12. The method of claim 11, further comprising:

coupling the first portion of the suture to the distal end portion of the dilator, the distal end portion of the dilator defining the aperture through which the first portion of the suture is disposed.

13. The method of claim 11, further comprising:

after the removing, trimming the portion of the implant extending through the bodily tissue such that the suture is detached from the implant.

14. The method of claim 11, wherein the pushing includes pushing the dilator into a portion of the body in a pelvic region of the patient.

15. The method of claim 11, wherein the pushing includes pushing the needle and the dilator into the body in a direction towards the supra-pubic incision, and the removing includes removing the dilator from the body via the supra-pubic incision by moving the dilator in a direction substantially the same as the direction used to push the dilator into the body.

16. The method of claim 11, wherein the pushing includes pushing the dilator into the body and through a portion of an obturator.

* * * * *